(12) United States Patent
Simanovsky et al.

(10) Patent No.: US 6,317,509 B1
(45) Date of Patent: *Nov. 13, 2001

(54) COMPUTED TOMOGRAPHY APPARATUS AND METHOD FOR CLASSIFYING OBJECTS

(75) Inventors: Sergey Simanovsky, Lynn; Ibrahim M. Bechwati, Roslindale; Muzaffer Hiraoglu, Woburn; Carl R. Crawford, Brookline, all of MA (US)

(73) Assignee: Analogic Corporation, Peabody, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/022,059

(22) Filed: Feb. 11, 1998

(51) Int. Cl.[7] .............................. G06K 9/00; G06K 9/56; G06K 9/42; A61B 6/00; G01T 1/166
(52) U.S. Cl. ........................ 382/131; 382/205; 382/257; 378/4; 250/363.04
(58) Field of Search ...................................... 382/131, 128, 382/132, 141, 143, 154, 149, 168, 205, 219, 256, 257, 260–265, 286, 308; 378/4, 21, 57, 901; 345/419, 420, 421, 423, 424; 250/363.04, 367, 390.04

(56) References Cited

U.S. PATENT DOCUMENTS

| | | | |
|---|---|---|---|
| 4,064,440 | 12/1977 | Roder | 250/367 |
| 4,366,382 | 12/1982 | Kotowski | 378/57 |
| 4,511,799 | 4/1985 | Bjorkholm | 250/367 |
| 4,729,098 | 3/1988 | Cline et al. | 345/421 |
| 4,835,688 | 5/1989 | Kimura | 345/424 |
| 4,903,202 | 2/1990 | Crawford | 382/131 |
| 4,905,148 | 2/1990 | Crawford | 382/131 |

(List continued on next page.)

FOREIGN PATENT DOCUMENTS

| | | | |
|---|---|---|---|
| 0 366 387 A2 | 10/1989 | (EP) . | |
| WO96/13017 | 5/1996 | (WO) | G06K/9/00 |

Primary Examiner—Amelia M. Au
Assistant Examiner—Mehrdad Dastouri
(74) Attorney, Agent, or Firm—McDermott, Will & Emery

(57) ABSTRACT

A method and apparatus detects sheet explosives in computed tomography (CT) data. In particular, sheet-shaped objects such as sheet explosives can be discriminated from other object shapes and detected. The detection includes analyzing a neighborhood of voxels surrounding a test voxel. If the density of the test voxel is sufficiently different from the mean density of the neighboring voxels, then it is concluded that the test voxel is associated with a sheet object. Sheet objects can also be detected by eroding the CT data so as to eliminate voxels associated with thin objects. Remaining objects are then subtracted from the original data, leaving only thin sheet-shaped objects. Erosion of the data can be performed by identifying a neighborhood of voxels surrounding a voxel of interest. If the number of voxels having densities below a predetermined threshold exceeds a predetermined number, then it is assumed that the test voxel is a surface voxel and is removed from the object. A connectivity process can be applied to voxels to combine them into objects after sheets are detected to prevent sheets from being inadvertently removed from the data by erosion. A dilation function can then be performed on the eroded object to replace surface voxels removed by erosion. A corrected mass using the mean eroded density of the object can be computed and compared to mass thresholds to classify the object as to whether it poses a threat. Multiple mass thresholds can be used, each of which is associated with a particular density range based on the density of an expected threat object.

24 Claims, 13 Drawing Sheets

U.S. PATENT DOCUMENTS

| | | | |
|---|---|---|---|
| 4,914,589 | * 4/1990 | Crawford | 382/131 |
| 5,022,062 | 6/1991 | Annis | 378/86 |
| 5,044,002 | 8/1991 | Stein | 378/54 |
| 5,098,640 | 3/1992 | Gozani et al. | 376/166 |
| 5,125,015 | 6/1992 | Shimoni et al. | 378/51 |
| 5,153,439 | * 10/1992 | Gozani | 250/390.04 |
| 5,166,876 | 11/1992 | Cline et al. | 345/424 |
| 5,182,764 | 1/1993 | Peschmann et al. | 378/57 |
| 5,206,592 | 4/1993 | Buess et al. | 324/307 |
| 5,233,300 | 8/1993 | Buess et al. | 324/307 |
| 5,291,402 | 3/1994 | Pfoh | 378/13 |
| 5,319,547 | 6/1994 | Krug et al. | 705/13 |
| 5,345,393 | 9/1994 | Ueda | 395/500.19 |
| 5,442,672 | * 8/1995 | Bjorkholm et al. | 378/4 |
| 5,479,023 | 12/1995 | Bartle | 250/390.04 |
| 5,490,218 | 2/1996 | Krug et al. | 382/100 |
| 5,506,785 | 4/1996 | Blank et al. | 700/98 |
| 5,528,703 | 6/1996 | Lee | 382/257 |
| 5,544,283 | 8/1996 | Kaufman et al. | 345/424 |
| 5,548,694 | 8/1996 | Frisken Gibson | 345/424 |
| 5,600,700 | 2/1997 | Krug et al. | 378/57 |
| 5,606,517 | 2/1997 | Traub et al. | 395/500.3 |
| 5,630,034 | 5/1997 | Oikawa et al. | 345/424 |
| 5,638,499 | 6/1997 | O'Connor et al. | 345/434 |
| 5,638,502 | 6/1997 | Murata | 345/435 |
| 5,642,393 | 6/1997 | Krug et al. | 378/57 |
| 5,642,394 | 6/1997 | Rothschild | 378/57 |
| 5,647,018 | 7/1997 | Benjamin | 382/128 |
| 5,699,400 | 12/1997 | Lee et al. | 378/57 |
| 5,712,926 | 1/1998 | Eberhard et al. | 382/205 |
| 5,724,493 | * 3/1998 | Hosoya et al. | 345/424 |
| 5,832,134 | * 11/1998 | Avinash et al. | 382/257 |
| 5,838,758 | * 11/1998 | Krug et al. | 378/53 |
| 5,841,832 | * 11/1998 | Mazess et al. | 378/56 |

\* cited by examiner

Initialize the number of assigned labels, $N_L = 0$
Initialize the label equivalency array, $l_{(i)} = i$
For slice number $k$ from 0 to $K-1$
  for row number $j$ from 0 to $J-1$
    for column number $i$ from 0 to $I-1$
      label voxel as background, $L(i,j,k) = 0$
      if voxel value is in the range of interest $p_l \leq C(i,j,k) \leq p_h$ then
        for all existing labeled *neighbors* of given *connectivity*
          if $\{C(i,j,k) - C(neighbor)\} < \triangle$ AND $L(neighbor) > 0$ then
            check if current voxel has already been labeled
            if $L(i,j,k) > 0$ then compare the current label to the neighbor's label
            if $L(i,j,k) \neq L(neighbor)$ then resolve labeling ambiguity
              follow the equivalency links to find the lowest possible equivalent
              label values for the current voxel ($l_c$) and for the neighbor ($l_n$)
              initialize the equivalent values. $l_c = L(i,j,k)$ and $l_n = L(neighbor)$
              while $l_c \neq l(l_c)$ do $l_c = l(l_c)$
              while $l_n \neq l(l_n)$ do $l_n = l(l_n)$
              if the lowest equivalent labels differ, establish new link towards
              the lower value and this value to label the current voxel

*FIG. 10*

```
            if l_c > l_n then
                    l(l_c) = l_n
                    L(i,j,k) = l_n
            endif
            if l_c < l_n then
                    l(l_n) = l_c
                    L(i,j,k) = l_c
            endif
        endif
        else assign neighbor's label to the current voxel
            L(i,j,k) = L(neighbor)
        endif
      endif neighbor's density checked
   endfor all neighbors checked
   if there are no labeled neighbors L(i,j,k) == 0 then
        increment the number of assigned labels N_L = N_L + 1
        assign a new label L(i,j,k) = N_L
   endif
  endif labeled current voxel of interest (i,j,k)
 endfor looped over all rows in slice k, row j
 endfor looped over all rows in slice k
endfor looped over all slices in the bag image
```

FIG. 10

*(CONTINUED FROM SHEET 10/13)*

COMPUTED TOMOGRAPHY APPARATUS AND METHOD FOR CLASSIFYING OBJECTS

RELATED APPLICATIONS

This patent application and/or patents is related to the following copending U.S. applications, of the same assignee as the present application, the contents of which are incorporated herein in their entirety by reference:

"Nutating Slice CT Image Reconstruction Apparatus and Method," invented by Gregory L. Larson, et al., U.S. application Ser. No. 08/831,558, filed on Apr. 9, 1997, now U.S. Pat. No. 5,802,134, issued on Sep. 1, 1998;

"Computed Tomography Scanner Drive System and Bearing," invented by Andrew P. Tybinkowski, et al., U.S. application Ser. No. 08/948,930, filed on Oct. 10, 1997, now U.S. Pat. No. 5,982,844, issued Nov. 9, 1999;

"Air Calibration Scan for Computed Tomography Scanner with Obstructing Objects," invented by David A. Schafer, et al., U.S. application Ser. No. 08/948,937, filed on Oct. 10, 1997, now U.S. Pat. No. 5,949,842, issued Sep. 7, 1999;

"Computed Tomography Scanning Apparatus and Method With Temperature Compensation for Dark Current Offsets," invented by Christopher C. Ruth, et al., U.S. application Ser. No. 08/948,928, filed on Oct. 10, 1997, now U.S. Pat. No. 5,970,113, issued Oct. 19, 1999;

"Computed Tomography Scanning Target Detection Using Non-Parallel Slices," invented by Christopher C. Ruth, et al., U.S. application Ser. No. 08/948,491, filed on Oct. 10, 1997, now U.S. Pat. No. 5,909,477, issued on Jun. 1, 1999;

"Computed Tomography Scanning Target Detection Using Target Surface Normals," invented by Christopher C. Ruth, et al., U.S. application Ser. No. 08/948,929, filed on Oct. 10, 1997, now U.S. Pat. No. 5,901,198, issued on May 4, 1999;

"Parallel Processing Architecture for Computed Tomography Scanning System Using Non-Parallel Slices," invented by Christopher C. Ruth, et al., U.S. application Ser. No. 08/948,697, filed on Oct. 10, 1997, U.S. Pat. No. 5,887,047, issued on Mar. 23, 1999;

"Computed Tomography Scanning Apparatus and Method For Generating Parallel Projections Using Non-Parallel Slice Data," invented by Christopher C. Ruth, et al., U.S. application Ser. No. 08/948,492, filed on Oct. 10, 1997, now U.S. Pat. No. 5,881,122, issued on Mar. 9, 1999;

"Computed Tomography Scanning Apparatus and Method Using Adaptive Reconstruction Window," invented by Bernard M. Gordon, et al., U.S. application Ser. No. 08/949,127, filed on Oct. 10, 1997;

"Area Detector Array for Computed Tomography Scanning System," invented by David A Schafer, et al., U.S. application Ser. No. 08/948,450, filed on Oct. 10, 1997;

"Closed Loop Air Conditioning System for a Computed Tomography Scanner," invented by Eric Bailey, et al., U.S. application Ser. No. 08/948,692, filed on Oct. 10, 1997, now U.S. Pat. No. 5,982,843, issued Nov. 9, 1999;

"Measurement and Control System for Controlling System Functions as a Function of Rotational Parameters of a Rotating Device," invented by Geoffrey A. Legg, et al., U.S. application Ser. No. 08,948,493, filed on Oct. 10, 1997, now U.S. Pat. No. 5,932,874;

"Rotary Energy Shield for Computed Tomography Scanner," invented by Andrew P. Tybinkowski, et al., U.S. application Ser. No. 08/948,698, filed on Oct. 10, 1997, now U.S. Pat. No. 5,937,028, issued Aug. 10, 1999;

"Apparatus and Method for Detecting Sheet Objects in Computed Tomography Data," invented by Muzaffer Hiraoglu, et al., U.S. application Ser. No. 09/022,189, filed on Feb. 11, 1998, now U.S. Pat. No. 6,111,974, issued on Aug. 29, 2000;

"Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000;

"Apparatus and Method for Combining Related Objects in Computed Tomography Data," invented by Ibrahim M. Bechwati, et al., U.S. appliation Ser. No. 09/022,060, filed on Feb. 11, 1998, now U.S. Pat. No. 6,128,365, issued on Oct. 3, 2000;

"Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Correcting Object Density in Computed Tomography Data," invented by Ibrahim M. Bechwati, et al., U.S. application Ser. No. 09/022,354, filed on Feb. 11, 1998, now U.S. Pat. No. 6,108,396, issued on Aug. 22, 2000;

"Apparatus and Method for Density Discrimination of Objects in Computed Tomography Data Using Multiple Density Ranges," invented by Sergey Simanovsky, et al., U.S. application Ser. No. 09/021,889, filed on Feb. 11, 1998, now U.S. Pat. No. 6,078,642, issued on Jun. 20, 2000;

"Apparatus and Method for Detection of Liquids in Computed Tomography Data," invented by Muzaffer Hiraoglu, et al., U.S. application Ser. No. 09/022,064, filed on Feb. 11, 1998, now U.S. Pat. No. 6,026,171, issued on Feb. 15, 2000;

"Apparatus and Method for Optimizing Detection of Objects in Computed Tomography Data," invented by Muzaffer Hiraoglu, et al., U.S. application Ser. No. 09/022, 062, filed on Feb. 11, 1998;

"Multiple-Stage Apparatus and Method for Detecting Objects in Computed Tomography Data," invented by Muzaffer Hiraoglu, et al., U.S. application Ser. No. 09/022, 164, filed on Feb. 11, 1998, now U.S. Pat. No. 6,035,014, issued on Mar. 7, 2000;

"Apparatus and Method for Detecting Objects in Computed Tomography Data Using Erosion and Dilation of Objects," invented by Sergey Simanovsky, et al., U.S. application Ser. No. 09/022,204, filed on Feb. 11, 1998, now U.S. Pat. No. 6,067,366, issued on May 23, 2000.

FIELD OF THE INVENTION

The present invention relates generally to computed tomography (CT) scanners and more specifically to a target detection apparatus and method in a baggage scanning system which utilizes CT technology.

BACKGROUND OF THE INVENTION

Various X-ray baggage scanning systems are known for detecting the presence of explosives and other prohibited items in baggage or luggage prior to loading the baggage onto a commercial aircraft. Since many explosive materials may be characterized by a range of densities differentiable from that of other items typically found in baggage, explosives are generally amenable to detection by X-ray equipment. A common technique of measuring a material's density is to expose the material to X-rays and to measure the amount of radiation absorbed by the material, the absorption being indicative of the density.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and these data are used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator, or it can be analyzed by computer. Thus, detection of suspected baggage can require very attentive operators. The requirement for such attentiveness can result in greater operator fatigue, and fatigue as well as any distractions can result in a suspected bag passing through the system undetected.

Techniques using dual energy X-ray sources are known for providing additional information about a material's chemical characteristics, beyond solely a density measurement. Techniques using dual energy X-ray sources involve measuring the X-ray absorption characteristics of a material for two different energy levels of X-rays. These measurements provide an indication of the material's atomic number in addition to an indication of the material's density. Dual energy X-ray techniques for energy-selective reconstruction of X-ray CT images are described, for example, in Alvarez, et al., "Energy-selective Reconstructions in X-ray Computerized Tomography", *Phys. Med. Biol.* 1976, Vol. 21, No. 5, 733–744; and U.S. Pat. No. 5,132,998.

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in copending U.S. patent application Ser. No. 08/671,202, entitled "Improved Dual Energy Power Supply," (Attorney Docket No. ANA-094) which is assigned to the same assignee as the present invention and which is incorporated herein in its entirety by reference.

Certain types of explosives present a particular challenge to baggage scanning systems because, due to their moldable nature, they may be formed into geometric shapes that are difficult to detect. Many explosives capable of significantly damaging an aircraft are sufficiently large in length, width, and height so as to be readily detectable by an X-ray scanner system regardless of the explosive's orientation within the baggage. Another problem with some explosives is that they can be hidden inside an object such as a piece of electronic equipment, e.g., a lap top computer. These can be difficult to detect with traditional line scanning techniques. Also, an explosive powerful enough to damage an aircraft may be formed into a relatively thin sheet that is extremely small in one dimension and is relatively large in the other two dimensions. The detection of explosives may be difficult because it may be difficult to see the explosive material in the image, particularly when the material is disposed so that the thin sheet is perpendicular to the direction of the X-ray beam as the sheet passes through the system.

A system using CT technology typically includes a CT scanner of the third generation type, which typically includes an X-ray source and an X-ray detector system secured to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source generates a fan-shaped beam, or fan beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of the linear array of detectors is relatively small in the Z-axis direction the fan beam is relatively thin in that direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from a point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well known algorithms, a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner.

Baggage scanners using CT techniques have been proposed. One approach, described in U.S. Pat. No. 5,182,764 (Peschmann et al.) and U.S. Pat. No. 5,367,552 (Peschmann et al.) (hereinafter the '764 and '552 patents), has been commercially developed and is referred to hereinafter as the "InVision Machine." The InVision Machine includes a CT scanner of the third generation type, which typically include an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

One important design criterion for a baggage scanner is the speed with which the scanner can scan an item of baggage. To be of practical utility in any major airport, a baggage scanner should be capable of scanning a large number of bags at a very fast rate. One problem with the InVision Machine is that CT scanners of the type described in the '764 and '552 patents take a relatively long time, e.g., from about 0.6 to about 2.0 seconds, for one revolution of the disk to generate the data for a single sliced CT image. Further, the thinner the slice of the beam through the bag for each image, the better the resolution of the image. The CT scanner should provide images of sufficient resolution to detect plastic explosives on the order of only a few millimeters thick. Therefore, to provide adequate resolution, many revolutions are required. To meet high baggage throughput rates, a conventional CT baggage scanner such as the InVision Machine can only afford to generate a few CT images per bag. Clearly, one cannot scan the entire bag within the time allotted for a reasonably fast throughput. Generating only a few CT images per baggage items leaves most of the item unscanned and therefore does not provide scanning adequate to identify all potential threat objects in the bag, such as sheets of explosive material.

To improve throughput, the InVision Machine uses a pre-screening process which produces a two-dimensional projection image of the entire bag from a single angle. Regions of the projection identified as potentially containing threat items can then be subjected to a full scan or manual inspection. With this pre-screening and selective region scanning approach, the entire bag is not scanned, thus allowing potential threat items to pass through undetected. This is especially true in the case of sheet items oriented transversely to the direction of propagation of the radiation used to form the pre-screen projection and where the sheet covers a relatively large portion of the area of the bag.

Another baggage scanning system is described in an International Patent Application under the Patent Cooperation Treaty, document number WO 96/13017, published on May 2, 1996, entitled, "X-Ray Computed Tomography (CT) System for Detecting Thin Objects," invented by Eberhard, et al.(referred to herein as the "Eberhard et al. system"). In the Eberhard, et al. system, an entire bag is subjected to a CT scan to generate voxel density data for the bag. A connected components labeling (CCL) process is then applied to the entire bag to identify objects by grouping voxels which are physically close together and which have densities within a predetermined range of densities. The voxels in each object are then counted to determine the volume of each object. If the volume of an object exceeds a threshold, the mass of the object is computed by multiplying the volume of each object voxel by its density and then totaling the individual voxel masses. If the mass of an object exceeds a mass threshold, the object is concluded to be a threat.

The Eberhard et al. publication teaches that its system can identify thin objects. The system sets its labeling density at a low level such that thin objects viewed edge-on which partially fill a voxel can be detected.

A significant drawback to the Eberhard et al. system is that it may miss thin objects such as sheet explosives that are not viewed edge-on and which cover a large area of the bag. These transversely oriented sheet objects will add only slightly to the density measured for the bag and will have only small density contrast with the background. If the density threshold used during CCL is set low enough to detect these sheets, then, because of the low contrast between the sheet and the background, the entire bag will be connected and labeled together, and no discernable object will be identified. If the threshold is set higher, then the sheet object will be missed.

It would be beneficial for the baggage scanning equipment to automatically analyze the acquired density data and determine if the data indicate the presence of any contraband items, e.g., explosives. This automatic explosive detection process should have a relatively high detection rate such that the chances of missing an explosive in a bag are small. At the same time, the false alarm rate of the system should be relatively low to substantially reduce or eliminate false alarms on innocuous items. Because of practical considerations of baggage throughput at large commercial airports, a high false alarm rate could reduce system performance speed to a prohibitively low rate. Also, it would be beneficial to implement a system which could distinguish among the different types of explosive, e.g., powders, bulks, sheets, etc., such that a detected threat can be more accurately characterized.

SUMMARY OF THE INVENTION

The present invention is directed to an object identification apparatus and method and a computed tomography (CT) baggage scanning system and method which use the object identification apparatus and method of the invention. The object identification apparatus and method of the invention analyze acquired CT density data for a region to detect objects in the data. The region can include at least a portion of the inside of a container such as a piece of baggage or luggage. Detected objects can then be labeled according to their physical configuration. For example, in one embodiment, objects can be labeled as being bulk objects or sheet objects. In one embodiment, after objects are detected and labeled, they are discriminated, that is, they are classified as being threat objects or non-threat objects.

In one embodiment, the invention uses a sheet detection process which identifies thin sheet-shaped objects. One form of sheet detection applies a statistical approach to determine whether each volume element or "voxel" in the density data is associated with a sheet object. Under this statistical approach, each voxel is analyzed by comparing its density to that of its neighboring voxels. In one embodiment, the mean and standard deviation of the densities of the neighboring voxels are computed. The difference between the density of the voxel being analyzed and the mean density of the neighboring voxels is compared to a predetermined threshold difference, which can be related to the standard deviation of the densities of the neighboring voxels. If the density of the voxel of interest differs from the mean density by more than the predetermined threshold difference, then it is concluded that the voxel of interest is associated with a thin object, e.g., a sheet.

The voxels can be analyzed one at a time and can be individually labeled according to whether they are associated with a sheet object. Next, the set of labeled voxels can be analyzed to group associated voxels into objects. In one embodiment, a standard connected components labeling (CCL) approach is used to group neighboring voxels of similar densities into sheets. Under this standard CCL approach, each voxel labeled as a sheet voxel is compared to neighboring sheet voxels to determine the difference between their densities. If the difference in density is below a predetermined density difference threshold, then it is assumed that the two neighboring voxels belong to the same object, i.e., sheet. This process continues until all voxels labeled as sheet voxels are combined into sheet objects. This may result in one or more sheet objects being identified within the data for a single region or bag.

The apparatus and method of the invention can also classify objects such as detected sheet objects as being threat objects or non-threat objects. In one embodiment, this is done by comparing the mass of the objects to a predetermined threshold mass. If the mass of an object is above the predetermined mass threshold, then it is concluded that the object is a threat object. When a bag is identified as containing a threat object, it can be marked for further analysis. The bag can be identified for further inspection by the operator or an image of the entire interior of the bag can be produced from the density data.

The present invention also provides for the identification and classification of bulk objects, such as bulk explosives, in the acquired CT density data for a region such as the interior of a piece of luggage or baggage. The bulk detection process of the invention uses a modified connected components labeling (CCL) process to identify bulk objects. Under standard CCL, neighboring voxels having density values which differ by less than a predetermined threshold are labeled as being part of the same object. Each voxel is analyzed and compared to its neighbors to combine the voxels into objects. This common CCL approach has a drawback in that objects that are close together or that touch each other and have similar densities may be combined into a single object. The modified CCL approach of the invention separates these objects into individually labeled objects.

The approach of the invention applies a "morphological" CCL method. Each object is first "eroded," by removing all of its surface voxels. This tends to separate connected objects into multiple individual objects. The separated objects are then separately labeled. Next, a "dilation" step is applied in which surface voxels are added back to identified and labeled objects. Hence, this morphological approach to CCL allows objects in close proximity to each other to be separately identified and labeled. The objects can then be separately discriminated and classified as being threats or non-threats.

Standard erosion approaches used in other image data processing settings can lead to undesirable results. For example, one standard erosion process identifies a surface voxel as being any voxel having at least one neighboring voxel whose density is below a predetermined threshold. This assumes that all the voxels being analyzed adjacent to a neighboring voxel below the threshold are surface voxels. These identified surface voxels are then removed from the object. A drawback to this approach is that there are circumstances under which a voxel that is not at the surface of the object will be removed. For example, an object with an interior void region, such as a cylindrical, stick-shaped object with an interior, axial, thin, cylindrical hole, will have voxels around the outside of the void region removed. The undesirable result is that the interior void region is enlarged by the erosion process.

In one aspect of the present invention, erosion is performed in such a way that the probability of removing a non-surface voxel is reduced. In this aspect of the invention, for each voxel, a plurality of neighboring voxels is identified. In one embodiment, the neighboring voxels define a three-dimensional subregion or neighborhood which surrounds the voxel of interest. The subregion can be cube-shaped. Each voxel in the subregion is analyzed to determine if its density is within one or more predetermined ranges of densities. For each voxel of interest, the number of voxels in the associated subregion whose densities fall within the predetermined range of densities is compared to a threshold. If the number is lower than the threshold, then it is concluded that the voxel of interest is an object surface voxel, and the voxel is removed from the object.

In one embodiment of the erosion process of the invention, the predetermined range of densities is determined based on the density of the voxel of interest. The range is selected to be a range that includes the density of the voxel of interest. In this case, the analysis then determines the number of voxels in the subregion that are in the same density range. If that number does not exceed a threshold, then it is concluded that the voxel of interest is at a surface of an object, and the voxel is removed from the object.

In one embodiment of the erosion process of the invention, the predetermined range of densities is selected from a plurality of ranges, each of which is defined based on a threat to be identified. In this embodiment, the density of the voxel of interest determines the potential threat material and, therefore, the selected density range. For example, if the density of the voxel of interest indicates that it is a bulk explosive material, the density range for a bulk explosive material is selected for analysis of the subregion surrounding the voxel of interest. If the number of voxels in the subregion that are within the range and are therefore part of the same bulk explosive object does not exceed the threshold, then the voxel of interest is concluded to be a surface voxel, and it is removed from the object. This approach to erosion in accordance with the invention reduces the possibility of enlarging interior voids in the object and increases the likelihood of removing only exterior surface voxels.

In another aspect of the invention, the dilation step of the morphological CCL approach is applied to produce a more accurate measure of the size and, therefore, the mass, of an object. Under this approach, when voxels are added back to the surface of an eroded object, the density assigned to the added voxel is the average eroded density of the bulk object. That is, the average density of all of the voxels of an eroded object is computed. During subsequent dilation, each voxel added to the surface of the eroded object is assumed to have a density at the average eroded density. This approach substantially reduces or eliminates the inaccuracies in object mass and density caused by the partial volume effect, which is caused by surface voxels averaging the density of the object and background contained within a single surface voxel.

In another aspect of the invention, sheet objects can be detected in the density data by using a morphology approach analogous to the morphological CCL applied in bulk object detection. Under this morphological sheet detection approach, all objects in the data are eroded a predetermined number of times such that all thin sheet shaped objects are eliminated from the data. The number of erosions performed is based on the number of erosions needed to eliminate sheet objects from the data, which is related to the thickness of a sheet. Each erosion can remove one layer of surface voxels. Therefore, the number of erosions is related to the expected thickness of a sheet and the size of a voxel. After all of the erosion steps are performed, the voxels remaining in the data are assumed to be associated with bulk objects. Then, dilation can be performed to restore the bulk objects to their original size. The data associated with these objects can then be eliminated from further processing. The original data, with the bulk objects removed, are then analyzed to label the sheet objects. The remaining voxels are analyzed one at a time such as by the CCL process to combine voxels into sheet objects and then label the sheet objects. Next, discrimination is performed on the sheet objects to classify them as threats or non-threats, such as by comparing the objects mass to a predetermined mass threshold. Sheets with masses above the threshold can be classified as threats.

An optional CCL step can be performed between the erosion steps and the dilation step to identify objects in the eroded data. Then, the subsequent dilation and subtraction steps may be performed only on objects which exceed a predetermined size or mass.

Hence, in accordance with the invention, at least two sheet detection processes can be applied to the data for a region to identify voxels associated with sheet-shaped objects. These two approaches include the CFAR method and the morphological erosion-dilation method described above. Either approach can produce a set of binary data associated with the voxels, which binary data define each voxel as either being part of a sheet or not being part of a sheet. After identifying sheet voxels, a voxel connection approach, such as the morphological CCL of the invention, standard CCL, or other connectivity method, is performed to connect the voxels into objects. Under this approach, because sheets are identified in the data before connecting voxels into objects, the object connection process does not eliminate sheets from the data and thereby make them impossible to detect. It should be noted that the connection approach can be applied to the binary data generated by the sheet detection method, or it can be applied to the product of the binary data and the density data, i.e., the density data for voxels identified as being sheet voxels.

In another aspect of the invention, separate objects which should be considered as a single threat are combined or merged. Certain threats include multiple objects, e.g., multiple stick-shaped objects bundled or otherwise coupled together. These objects can be separated from each other during the erosion step of the morphological CCL process and, as a result, can be considered separate objects, each of which taken alone would not be classified as a threat under mass thresholding. However, when these objects are combined, they do pose a threat and should be classified as such. A merging process of the invention identifies such separated objects and combines them such that they can be identified as a threat.

In one embodiment, the merging process of the invention identifies objects that are close to each other and also have similar or equal densities and combines them into a single object. In one embodiment, a bounding box is computed for each object. The objects are compared for similar densities. If the difference in object densities is below a predetermined threshold and the absolute density of one or both of the objects is within a predetermined density range defining multiple-object threats, then the distance between the bounding boxes is determined. If the distance between bounding boxes is below a predetermined threshold and the objects are considered to be in close enough proximity to be considered a single object, then it is concluded that the objects should be combined into a single object. A total mass of all of the individual objects is computed and compared to the threat mass threshold. If the total mass exceeds the threshold, then the combined object is concluded to be a threat.

In another aspect, the invention can merge multiple small sheet objects into a single sheet object. In accordance with the invention, analysis of three-dimensional CT images of actual bags, as opposed to the partial or two-dimensional analysis of the prior art, has identified the effect that a high density object such as a metallic bar can obscure and/or interrupt the image of a large sheet, making it appear as multiple images of separate individual sheets. As a result, the single large sheet object can be identified as multiple smaller objects. The multiple smaller objects may be small enough, i.e., have low enough mass, such that all of them will be classified as non-threat items. This is especially a problem where the object should be classified as a threat and would be so classified if the system recognized it as a single object, instead of multiple separate objects. To solve this problem, in one aspect of the present invention, each sheet object is associated with a plane. Where multiple sheets are detected in the data, the planes for each sheet are examined in three-dimensional space. If the planes intersect and their intersection is close to the sheets, then it is concluded that the individual sheets are actually part of a larger sheet. The masses of the individual sheets are combined into a single value which is compared to the mass threshold during discrimination. If the mass of the combined sheet exceeds the mass threshold, then it is concluded that the sheet is a threat.

As mentioned above, after objects are identified in the density data, they are classified as to whether they are to be considered threats. In general, mass discrimination is used to classify the objects. In one embodiment, the mass of each identified object is computed by multiplying the density of each voxel by its volume and then totaling all of the individual voxel masses. The total object mass is then compared to a mass threshold. If the mass of the object exceeds the threshold, then it is concluded to be a threat object.

In the present invention, the mass threshold used for an object can be determined based on the type of object. That is, different mass thresholds are used for different types of objects. For example, a sheet object may be compared to one threshold while a powder explosive may be compared to a different mass threshold. This is due to the fact that different explosives pose different threats depending upon their masses. A large amount of one type of explosive may not pose as serious a threat as a smaller amount of a different type of explosive. Hence, in the present invention, mass thresholds can be selected based on the type of explosive. In one embodiment, the selection of mass threshold is determined by the density of the identified object, since it is the density that is closely related to the type of object identified. That is, the density of one type of explosive is in general different from the density of another type of explosive. These individual densities are used to identify the type of explosive and, therefore, determine the mass threshold to be used in classifying an object as a threat. This density-dependent mass thresholding of the invention provides a much more accurate threat classification than prior systems which use a single mass threshold for all objects.

In another aspect of the invention, calculation of the total mass of an object is enhanced to improve the threat classification accuracy of the system. As described above, using the modified CCL of the invention described herein, surface voxels of an object can be eroded from the object. In accordance with the invention, an erosion step can be performed to eliminate the effects of partial volume voxels located at the surface of the object. These voxels introduce inaccuracies because their density values contain density contributions from both the object and the background at the boundary of the object. In this aspect of the invention, erosion is performed to remove the surface voxels. Next, an average eroded density for the remaining object voxels is computed. The average eroded density is the average of the voxel densities remaining in the object after the erosion step. Next, the eroded surface voxels are replaced with voxels having density values equal to the average eroded density. The total mass can then be computed for the object using the surface voxels having the average eroded density value. This corrected total object mass provides more accurate classification of objects during subsequent mass discrimination.

In another aspect of the invention, separation between multiple objects in close proximity to each other is improved during the CCL process by careful tailoring of the acceptable density range for an object voxel. In one embodiment, accepted densities are defined in multiple density ranges with gaps between them in which densities would not be accepted to associate the voxel with an object of interest. That is, voxels having densities in the gaps are rejected and voxels within one of the density ranges are accepted as belonging to objects of interest. The accepted density ranges can be selected according to densities of known threat objects. For example, a density range may be selected for each of several different types of known explosives. In one embodiment, a gap between density ranges is selected to coincide with the expected density of typical surface voxels. By rejecting these surface voxels, multiple adjacent objects which would otherwise be combined and labeled as a single object are separated and labeled as individual objects. As separate objects, they can be independently analyzed and classified according to the level of threat they pose. Hence, the use of multiple density ranges allows for more accurate classification.

In yet another aspect of the invention, it might be the case that a liquid material does not pose a threat and should be classified as a non-threat object. Accordingly, the object identification and classification system of the invention can recognize and identify liquids in containers such that they can be eliminated as threats. This provides a method of discriminating detected objects beyond the mass and density discrimination approaches of the invention described above.

In one embodiment, the invention determines whether an object is a contained liquid by first creating a bounding box which surrounds the object. The numbers of voxels close to each of the surfaces of the bounding box are computed. The top surface of the liquid is then identified by identifying a horizontal surface of the bounding box. The ratio of voxels close to the top surface to the total number of surface voxels can then be calculated. If the fraction of top surface voxels exceeds a predetermined threshold ratio, and if the density of voxels above the top surface indicates that air is located above the top surface, then it is concluded that the object is a contained liquid. In one embodiment, it can then be concluded that the object does not pose a threat.

In another embodiment, the invention applies a statistical approach to determining whether an object in the bounding box is a contained liquid. Along a line between the top and bottom of the bounding box, a histogram of the top-surface voxels and a histogram of the bottom-surface voxels are computed. The peak in the top-surface histogram indicates the vertical position of the top-surface voxels, and the peak in the bottom-surface histogram indicates the vertical position of the bottom-surface voxels. If the ratio of the number of top-surface voxels to the top-surface area in the bounding box exceeds a threshold and the ratio of the number of top-surface voxels to bottom-surface voxels exceeds another threshold, then it can be concluded that the object is a contained liquid.

In still another aspect of the invention, detection is carried out in multiple paths or stages such that the overall detection process is more efficient. Each item that can be identified by the method of the invention is, in general, associated with a unique set of detection steps. Under a typical detection approach, all of the acquired CT density data would be subjected to each detection approach in series. It will be appreciated that this can be very time consuming. In addition, when an object is analyzed in accordance with one particular approach and is classified according to the threat it poses or by its object type, inefficiencies are introduced when that set of data is reanalyzed under the other remaining detection processes. In the present invention, a multi-path or multi-stage detection approach is used to eliminate these inefficiencies. Specific detection steps used to identify specific items are applied separately and, in one embodiment, in parallel. In one particular embodiment of this multiple-path method of the invention, where one specific detection path has been applied to a set of data and has classified a portion of the data, the classified portion of data are removed from further processing. This eliminates inefficiencies introduced by unnecessary re-analysis of data that has already been classified.

The present invention also allows for optimization of overall system detection rate (probability of detection) and false alarm rate. Each item that can be detected by the system of the invention is associated with an individual detection rate and false alarm rate. For example, sheet explosive detection has a unique probability of detection and false alarm rate. Also, each individual explosive material type has its own unique probability of detection and false alarm rate. The overall system probability of detection is an accumulation of each individual detection rate; in one embodiment, it is the average of the individual detection rates. In addition, the overall false alarm rate of the system is an accumulation of all of the individual false alarm rates; in one embodiment, it is the sum of the individual false alarm rates. In the present invention, the overall detection rate can be optimized by adjusting one or more or the individual detection rates. Also, the overall false alarm rate can be optimized by adjusting one or more of the individual false alarm rates. Hence, overall system performance can be adjusted as required to attain desired overall detection rate and/or false alarm rate by making adjustments to individual detection rates and/or false alarm rates.

It is possible that one or more individual detection rates can be lower than a specified overall detection rate. The system can provide the flexibility of adjusting one or more individual detection rates to a lower level while maintaining the overall rate within specified limits. Reducing one detection rate can also reduce the associated false alarm rate.

Thus, the overall system false alarm rate can be reduced while maintaining the overall system detection rate within the specified limits. Also, the overall detection rate can be maintained at a particular value while individual and/or overall system false alarm rates can be adjusted to desired levels.

The present invention provides substantial advantages over prior systems mentioned above in addition to the aforementioned advantages. For example, the system of the invention can provide a complete CT scan of a bag such that complete three-dimensional image data for the bag can be analyzed. This results in the system's ability to detect objects such as thin sheets in the bag regardless of orientation and size. In the InVision Machine, only regions identified as suspect by the 2D pre-screen are subjected to 3D scanning. Also, in one embodiment of the invention, voxels are not connected and identified as objects until voxels belonging to thin sheet objects are first identified. This eliminates the problems of identifying sheets found in systems such as the Eberhard et al. system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10 contains pseudocode which describes one embodiment of a modified connected component labeling method in accordance with the present invention.

DETAILED DESCRIPTION OF PREFERRED EMBODIMENTS OF THE INVENTION

The present invention provides an apparatus and method which detect, identify and/or classify objects in CT data for a region. The region can include the interior of a piece of baggage or luggage being carried or checked onto a commercial aircraft. The invention can therefore be implemented in a CT baggage scanning system. The objects identified by the invention can be objects known to pose threats to persons at an airport or on board an aircraft. These objects can include explosive objects and materials.

It should be noted that the explosive objects and materials that can be detected by the invention can be of various shapes and materials. The explosives can be commercial, military or improvised, i.e., home made. For example, explosive objects can be in various shapes including, but not limited to, sheets, single cylindrical containers or other such shapes, multiple cylinders or other stick shapes, and other bulk shapes. Various types of explosive materials formed or contained in these shapes can be detected in accordance with the invention.

Throughout the following description, it is noted that many thresholds, such as density thresholds, mass thresholds, density-dependent mass thresholds, and difference thresholds as well as process parameters are used to carry out the various methods of the invention. These thresholds and parameters are determined based on extensive analysis of the CT data, such as actual three-dimensional CT density data, for many actual threat and non-threat objects. This analysis included statistical analysis of the data employing statistical methods such as simulated annealing and genetic algorithms. In accordance with the invention, this analysis allows for threshold and/or parameter selection based on a particular objective to be met, e.g., false alarm and/or detection rate setting/optimization, discrimination of explosive type, etc., as described below.

Figure 1:
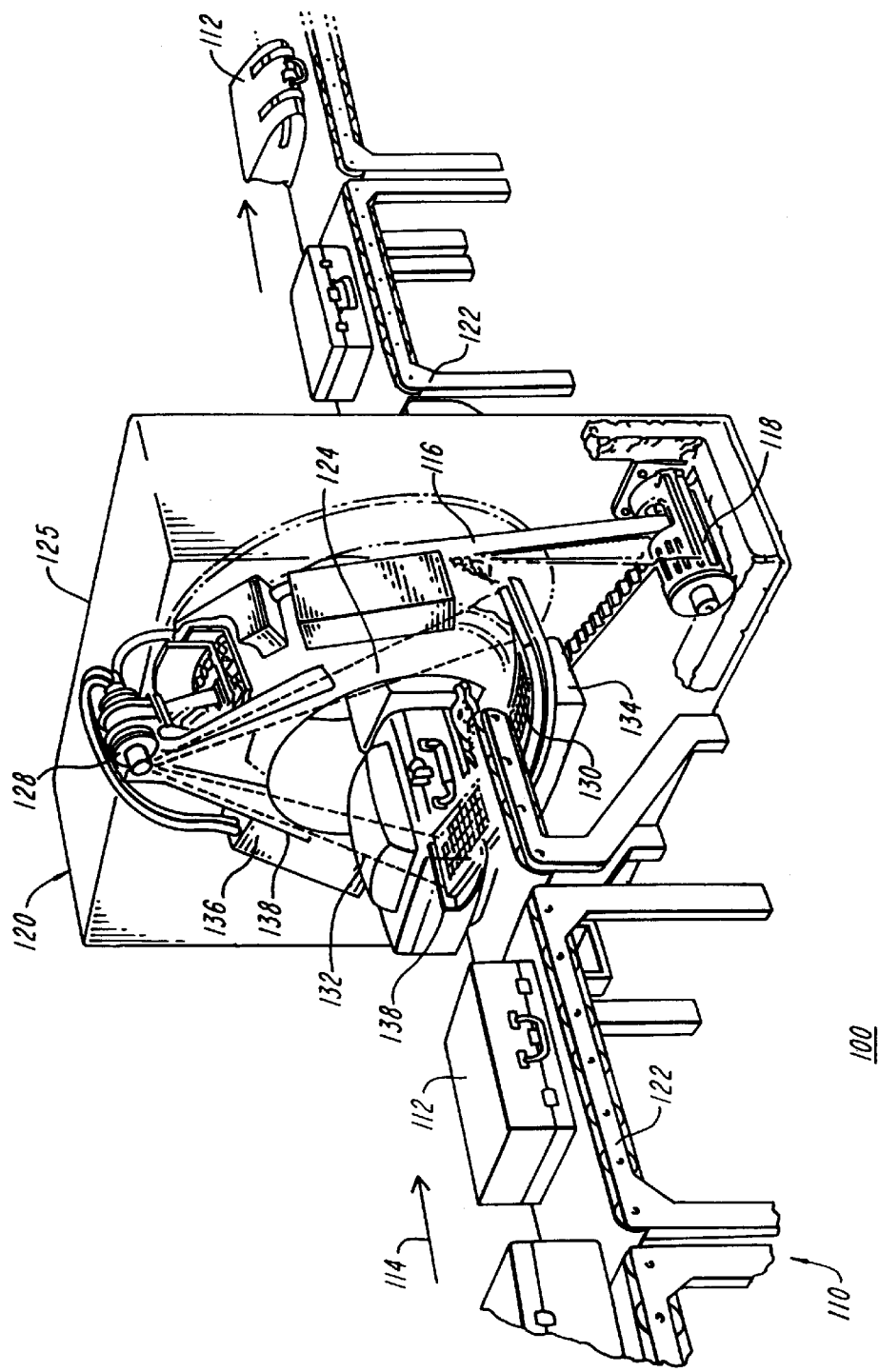
FIG. 1 contains a perspective view of a baggage scanning system in accordance with the present invention.
Figure 2:
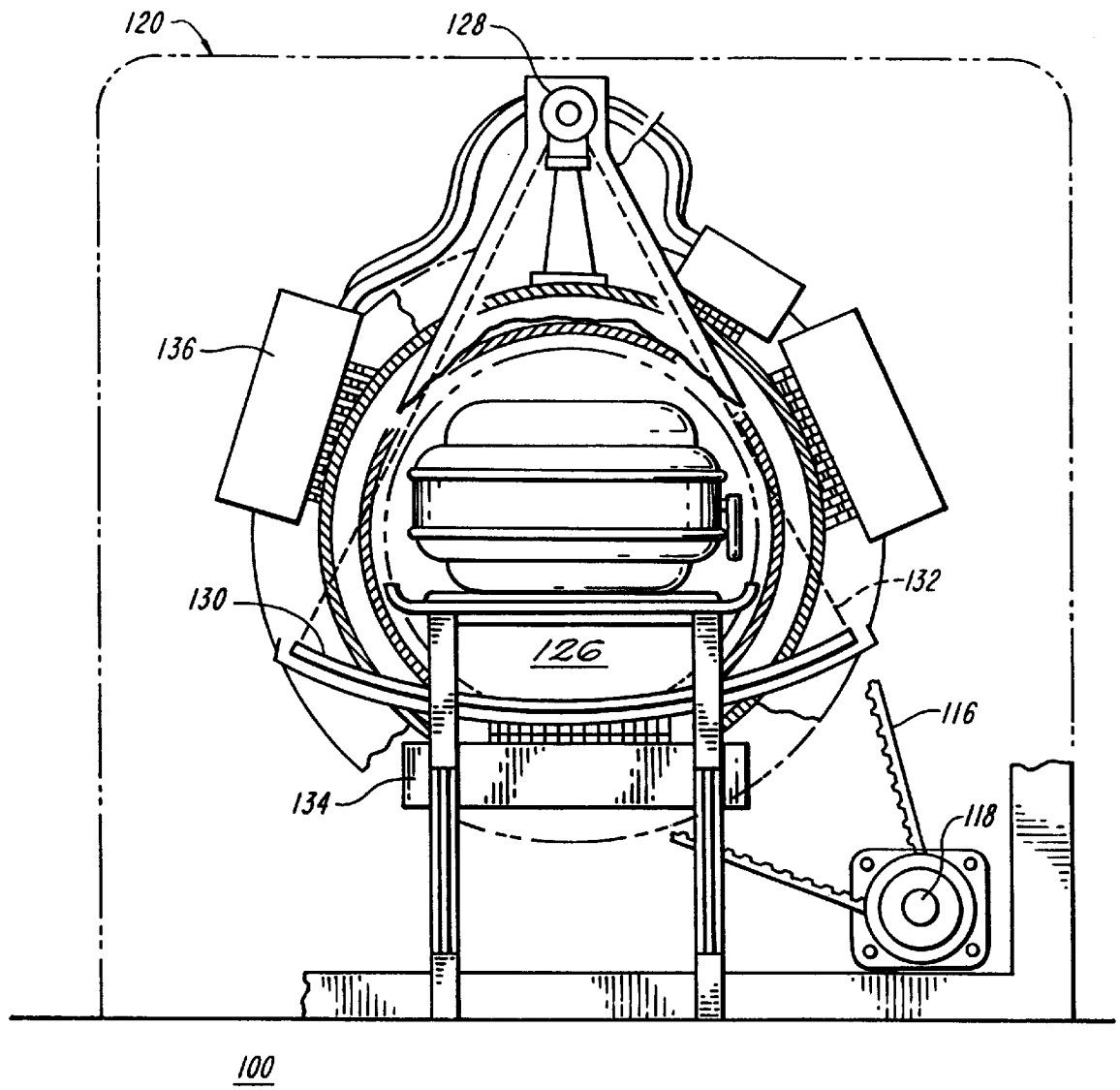
FIG. 2 contains a cross-sectional end view of the system shown in FIG. 1.
Figure 3:
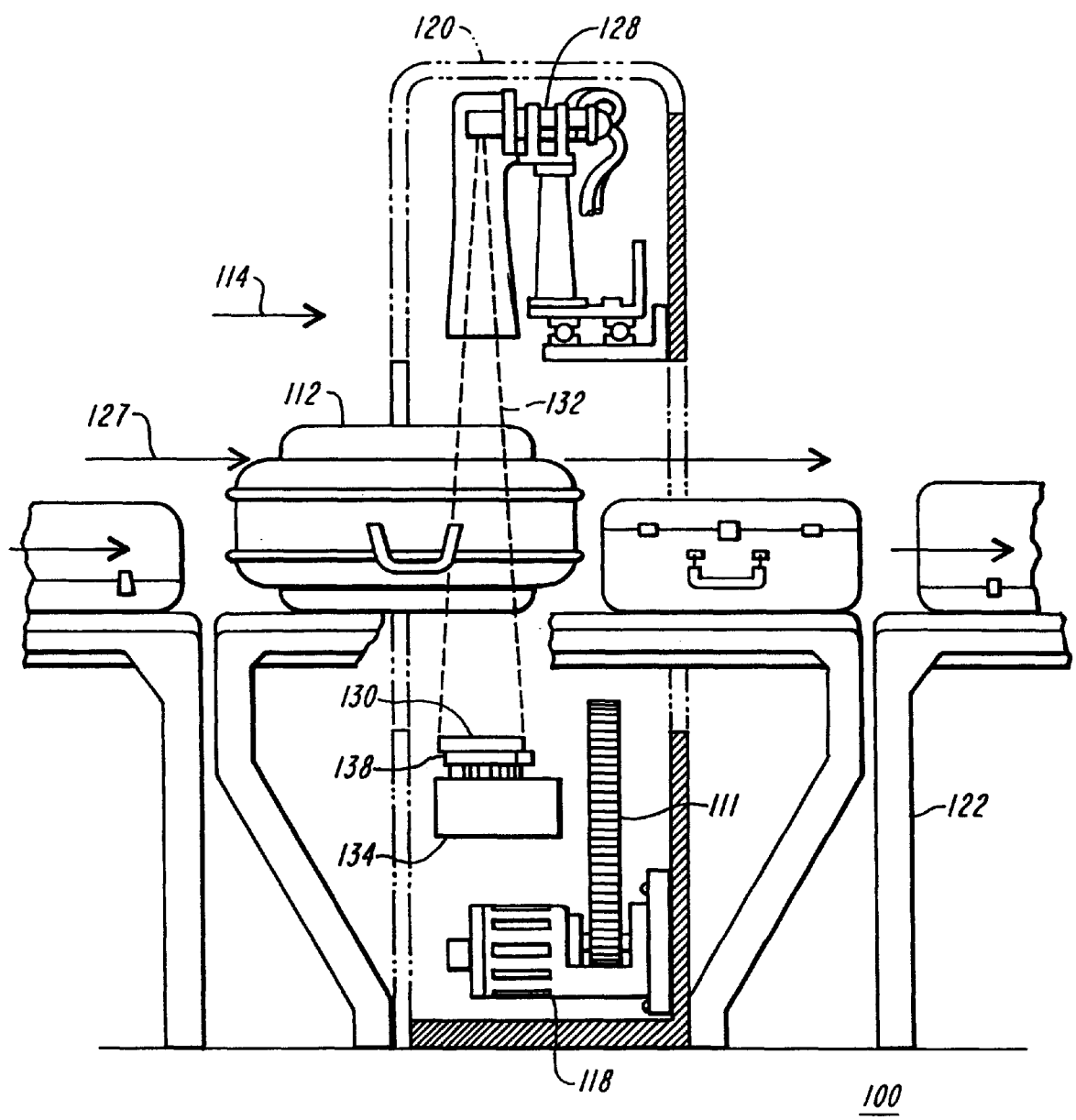
FIG. 3 contains a cross-sectional radial view of the system shown in FIG. 1.

FIGS. 1, 2 and 3 contain perspective, end cross-sectional and radial cross-sectional views, respectively, of a baggage scanning system 100 constructed in accordance with the invention, which provides object detection, identification and classification in accordance with the invention. The baggage scanning system 100 generates CT data for a region which can include a piece of baggage. The system can use the CT data to generate image volume elements or "voxels" for the region. The baggage scanning system can be of the type described in copending U.S. patent application Ser. No. 08/831,558, 08/948,930, 08/948,937, 08/948,928, 08/948,491, 08/948,929, 08/948,697, 08/948,492, 08/949,127, 08/948,450, 08/948,692, 08/948,493, 08/948,698, mentioned above and incorporated by reference.

The system 100 includes a conveyor system 110 for continuously conveying baggage or luggage 112 in a direction indicated by arrow 114 through a central aperture of a CT scanning system 120. The conveyor system includes motor driven belts for supporting the baggage. Conveyor system 110 is illustrated as including a plurality of individual conveyor sections 122; however, other forms of conveyor systems may be used.

The CT scanning system 120 includes an annular shaped rotating platform or disk 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," (Attorney Docket No. ANA-30CON) which is assigned to the assignee of the present application and which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 can be a two-dimensional array such as the array described in a copending U.S. patent application Ser. No. 08/948,450 entitled, "Area Detector Array for Computed Tomography Scanning System," (Attorney Docket No. ANA-137) filed on Oct. 10, 1997. The system 120 further includes a data acquisition system (DAS) 134 for receiving and processing CT data signals generated by detector array 130, and an X-ray tube control system 136 for supplying power to, and otherwise controlling the operation of, X-ray tube 128. The system 120 is also preferably provided with a computer processing system for processing the output of the data acquisition system 134 and for generating the necessary signals for operating and controlling the system 120. The computer system can also include a monitor for displaying information including generated images. The X-ray tube control system 136 can be a dual-energy X-ray tube control system such as the dual-energy X-ray tube control system described in the copending U.S. patent application Ser. No. 08/671,202 entitled, "Improved Dual Energy Power Supply," (Attorney Docket No. ANA-094), which is assigned to the same assignee as the present application and which is incorporated herein in its entirety by reference. Dual energy X-ray techniques for energy-selective reconstruction of X-ray CT images are particularly useful in indicating a material's atomic number in addition to indicating the material's density, although it is not intended that the present invention be limited to this type of control system. It is noted that the detailed description herein of the object identification and classification system and method of the invention describes the details in connection with single-energy data. It will be understood that the description is applicable to multiple-energy techniques. System 120 also includes shields 138, which may be fabricated from lead, for example, for preventing radiation from propagating beyond gantry 125.

In one embodiment, the X-ray tube 128 generates a pyramidically shaped beam, often referred to as a "cone beam," 132 of X-rays that pass through a three-dimensional imaging field, through which baggage 112 is transported by conveying system 110. After passing through the baggage disposed in the imaging field, cone beam 132 is received by detector array 130 which in turn generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the baggage is continuously transported through central aperture 126 by conveyor system 110 so as to generate a plurality of projections at a corresponding plurality of projection angles.

In a well known manner, signals from the detector array 130 can be initially acquired by data acquisition system 134, and subsequently processed by a computerized processing system using CT scanning signal processing techniques. The processed data can be displayed on a monitor, and/or can also be further analyzed by the processing system as described in detail below to determine the presence of a suspected material. For example, the CT data can be analyzed to determine whether the data suggest the presence of material having the density (and when a dual energy system is used, molecular weight) of explosives. If such data are present, suitable means can be provided for indicating the detection of such material to the operator or monitor of the system, for example, by providing an indication on the screen of the monitor by sounding an audible or visual alarm, and/or by providing an automatic ejection device (not shown) for removing the suspect bag from the conveyor for further inspection, or by stopping the conveyor so that the suspect bag can be inspected and/or removed.

As stated above, detector array 130 can be a two-dimensional array of detectors capable of providing scan data in both the directions of the X- and Y- axes, as well as in the Z-axis direction. During each measuring interval, the plurality of detector rows of the array 130 generate data from a corresponding plurality of projections and thereby simultaneously scan a volumetric region of baggage 112. The dimension and number of the detector rows are preferably selected as a function of the desired resolution and throughput of the scanner, which in turn are a function of the rotation rate of rotating platform 124 and the speed of conveying system 110. These parameters are preferably selected so that in the time required for a single complete rotation of platform 124, conveying system 110 advances the baggage 112 just enough so that the volumetric region scanned by detector array 130 during one revolution of the platform is contiguous and non-overlapping with (or partially overlapping with) the volumetric region scanned by detector array 130 during the next revolution of the platform.

Conveying system 110 continuously transports a baggage item 112 through CT scanning system 120, preferably at constant speed, while platform 124 continuously rotates at a constant rotational rate around the baggage items as they pass through. In this manner, system 120 performs a helical volumetric CT scan of the entire baggage item. Baggage scanning assembly 100 preferably uses at least some of the data provided by the array 130 and a helical reconstruction algorithm to generate a volumetric CT representation of the entire baggage item as it passes through the system. In one embodiment, the system 100 performs a nutating slice reconstruction (NSR) on the data as described in copending U.S. patent application Ser. No. 08/831,558, filed on Apr. 10, 1997, entitled, "Nutating Slice CT Image Reconstruction Apparatus and Method," (Attorney Docket No. ANA-118) of common assignee, and incorporated herein by reference. The system 100 thus provides a complete CT scan of each bag, rather than only providing CT scanning of selected portions of baggage items, without the need for a pre-screening device. The system 100 also provides rapid scanning since two-dimensional detector array 130 allows the system 100 to simultaneously scan a relatively large portion of each baggage item with each revolution of the platform 124.

Figure 4:
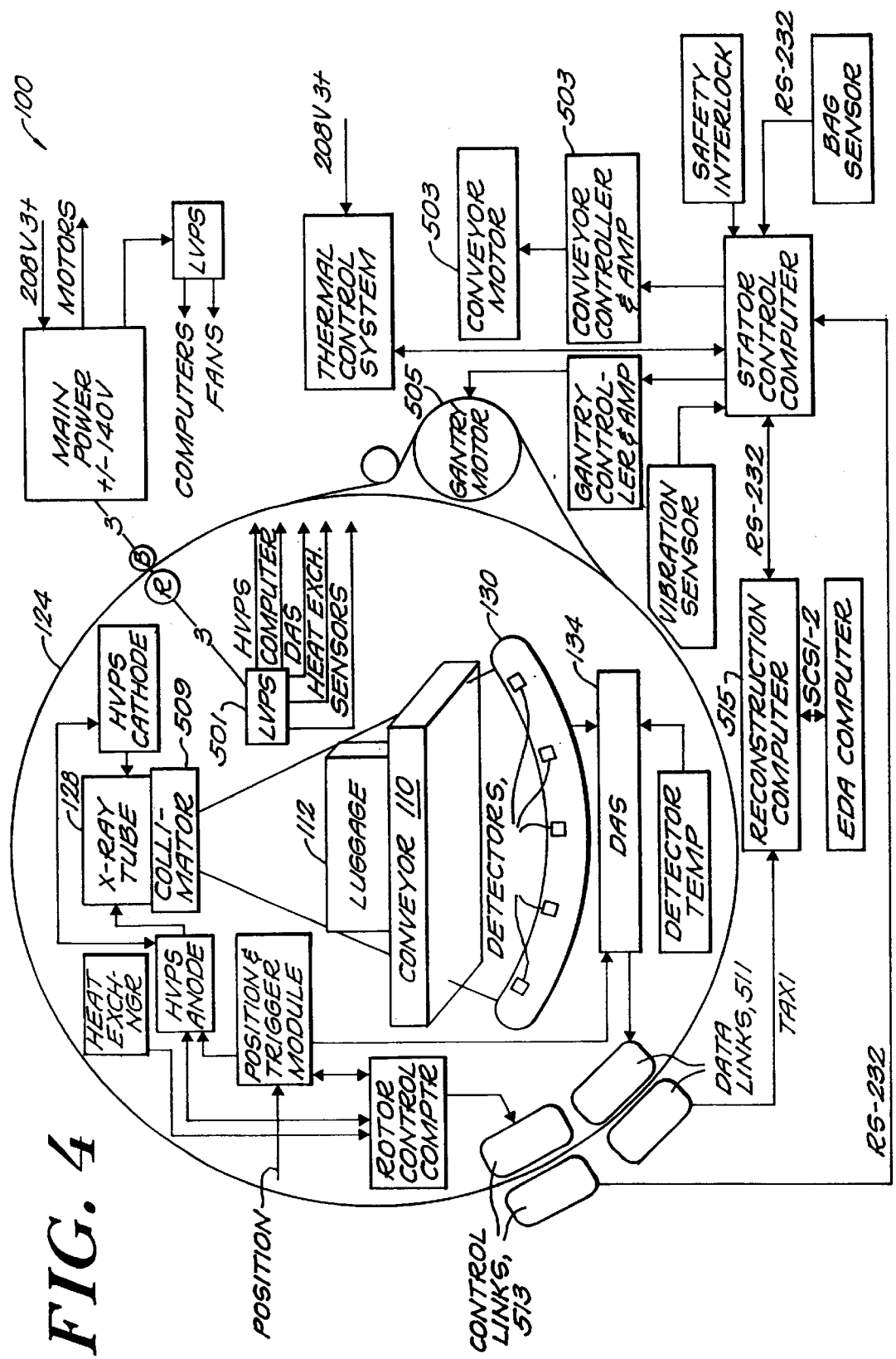
FIG. 4 contains a schematic electrical and mechanical block diagram of one embodiment of the baggage scanner of the invention.

FIG. 4 contains a mechanical/electrical block diagram of one embodiment of the baggage scanning system 100 of the invention. The mechanical gantry of the scanner 100 includes two major components, the disk 124 and the frame (not shown). The disk 124 is the rotational element which carries the X-ray assembly, the detector assembly 130, the data acquisition system (DAS) 134, a high-voltage power supply and portions of the monitor/control assembly, the power supply assembly and the data link assembly. The frame supports the entire system 100, including the baggage handling conveyor system 110. The disk 124 is mechanically connected to the frame via a duplex angular contact ball bearing cartridge. The disk 124 can be rotated at a constant rate by a belt which can be driven by a DC servomotor 505. The gantry also contains X-ray shielding on the disk and frame assemblies.

In one embodiment, the baggage conveyor system 110 includes a single belt driven at a constant rate to meet specified throughput requirements. The belt can be driven by a high-torque, low-speed assembly to provide a constant speed under changing load conditions. A low-attenuation carbon graphite epoxy material can be used for the portion of the conveyor bed in the X-ray. The total length of the conveyor is designed to accommodate three average length bags. A tunnel is used around the conveyor to meet the appropriate safety requirements of a cabinet X-ray system.

In one embodiment, input power of 208 volts, 3-phase, 30 amps services as the main supply which can provide power for the entire system. This input power can be supplied by the airport at which the system is installed. Power is transferred from the frame through a series of frame brushes which make continuous contact with the metal rings mounted to the disk 124. The low-voltage power supply 501 on the disk 124 provides power for the DAS 134, the X-ray cooling system and the various monitor/control computers and electronics. A low-voltage power supply on the frame provides power for the reconstruction computer and the various monitor/control electronics. The conveyor motor 503, the gantry motor 505, the high-voltage power supply and the X-ray coolant pump can all be supplied power directly from the main supply.

The high-voltage power supply provides power to the X-ray tube 128. The supply can provide a dual voltage across the cathode/anode. The driving waveform can be any desirable shape, and preferably is in the form of a sine wave. This supply can also provide X-ray filament power. The supply current can be held approximately constant for both voltages.

The dual-energy X-rays strike the baggage, and some portion of the X-rays pass through and strike the detector assembly 130. The detector assembly 130 performs an analog conversion from X-ray to visible photons and then to electrical current. The DAS 134 can sample the detector currents, multiplex the amplified voltages to a set of 16-bit analog-to-digital converters and multiplex the digital outputs to the computerized processing system 515, which generates CT data and processes the data in accordance with the invention as described below to detect, identify and classify objects in the piece of baggage 112. In one embodiment, the digital data from the DAS 134 are transferred to the processing system 515 via a non-contact serial data link 511. The DAS 134 can be triggered by the angular position of the disk 124.

The non-contact links 511 and 513 can transfer the high-speed digital DAS data to the processing system 515 and the low-speed monitor/control signals back and forth between the disk and frame control computers. The data link 511 can be based upon an RF transmitter and receiver.

In one embodiment, the image reconstructor portion of the processing system 515 converts the digital line integrals from the DAS 134 into a set of two-dimensional images of bag slices for both the high and low energies. The CT reconstruction can be performed via a helical-cone-beam solution, such as the nutating slice reconstruction method described in copending U.S. patent application Ser. No. 08/831,558, incorporated by reference above. The reconstructor can include embedded software, a high-speed DAS port, an array processor, a DSP-based convolver, an ASIC-based backprojector, image memory, UART control port, and a SCSI output port for image data. The array processor can perform data corrections and interpolation. The reconstructor can be self-hosted and can tag images based upon the baggage information received over the UART interface to the frame computer.

The processing system 515 can include a PC-based embedded control system. All subsystems can be monitored for key health and status information. This system can also control both motion systems, can sense baggage information, can control the environment, e.g., temperature, humidity, etc., can sense angular position of the disk 124 and can trigger the DAS and HVPS. This system can also have a video and keyboard interface for engineering diagnostics and control. Additionally, a control panel can be included for field service.

Most types of explosive objects can be grouped into a number of categories which can be based upon their shapes and/or constituent materials. For example, categories can include sheets, sticks, bulks and other categories based on shapes. Certain types of materials can be subdivided into subtypes which can also be based on containers such as cylinders. These categories have different typical features, such as shape, size, mass or density. In general, a single detection approach, such as the prior approaches referred to above, cannot detect all of these explosive types efficiently. In one embodiment, the invention can include multiple separate detection paths, which can include a separate path for each type. For example, the method can include a sheet explosive path and a path for the rest of the explosive objects which are referred to as "bulks" throughout this application.

In one embodiment of the object detection method and apparatus of the invention, the process begins by first performing a partial discrimination on the data to identify sheet-shaped objects. Next, a connection step such as some form of CCL is performed to connect objects. Then, further discrimination is performed to classify identified objects according to potential threats. This is in contrast to prior systems such as the Eberhard et al. system which perform connection first and then discrimination, resulting in the loss of thin sheet-shaped objects.

The basic steps of a method in accordance with one aspect of the invention include sheet explosive detection, bulk explosive detection, and discrimination. In one embodiment, the sheet detection and bulk detection can be performed respectively along two parallel paths. In one embodiment, sheet explosive detection is based on a process known as a constant false alarm rate method (CFAR) and modified in accordance with the invention, which statistically decides whether a volume element or voxel belongs to a sheet explosive. Sheet voxels can also be identified by a morphological sheet detection approach in accordance with the invention described below in detail. In one embodiment, the voxels identified as sheet voxels by CFAR or the morphological sheet detection of the invention are then connected and labeled using a standard connected component labeling (CCL) process. In another embodiment, the voxels are connected and labeled using the morphological CCL of the invention described herein. The labeled objects can then be discriminated by their mass. If the mass of an object is greater than a predetermined threshold, the object is declared a sheet explosive.

In one embodiment of the invention, bulk explosive detection uses a modified connected component labeling (CCL) process that can include morphological operations (erosion and dilation) to prevent objects growing together. In one embodiment, because sheets are detected on a separate analysis path, they need not be preserved in the erosion and dilation steps. Bulk detection can also involve controlled object merging for closely spaced threat objects, e.g., individual stick-shaped objects which should be considered as a single object. Discrimination is based on the density and mass of a detected object. In one embodiment, the mass thresholds for discrimination are density dependent. Lower density objects can be assigned higher mass thresholds for several reasons. For example, data indicate that the amount of low-density explosive required to cause a particular amount of damage is greater than the amount of high-density explosive. Therefore, at lower densities, a higher amount, i.e., higher mass, of material is required to trigger an alarm condition. Also, at low densities, a higher rate of false alarms may result. Accordingly, a higher mass threshold can reduce the number of false alarms at low densities.

Figure 5:
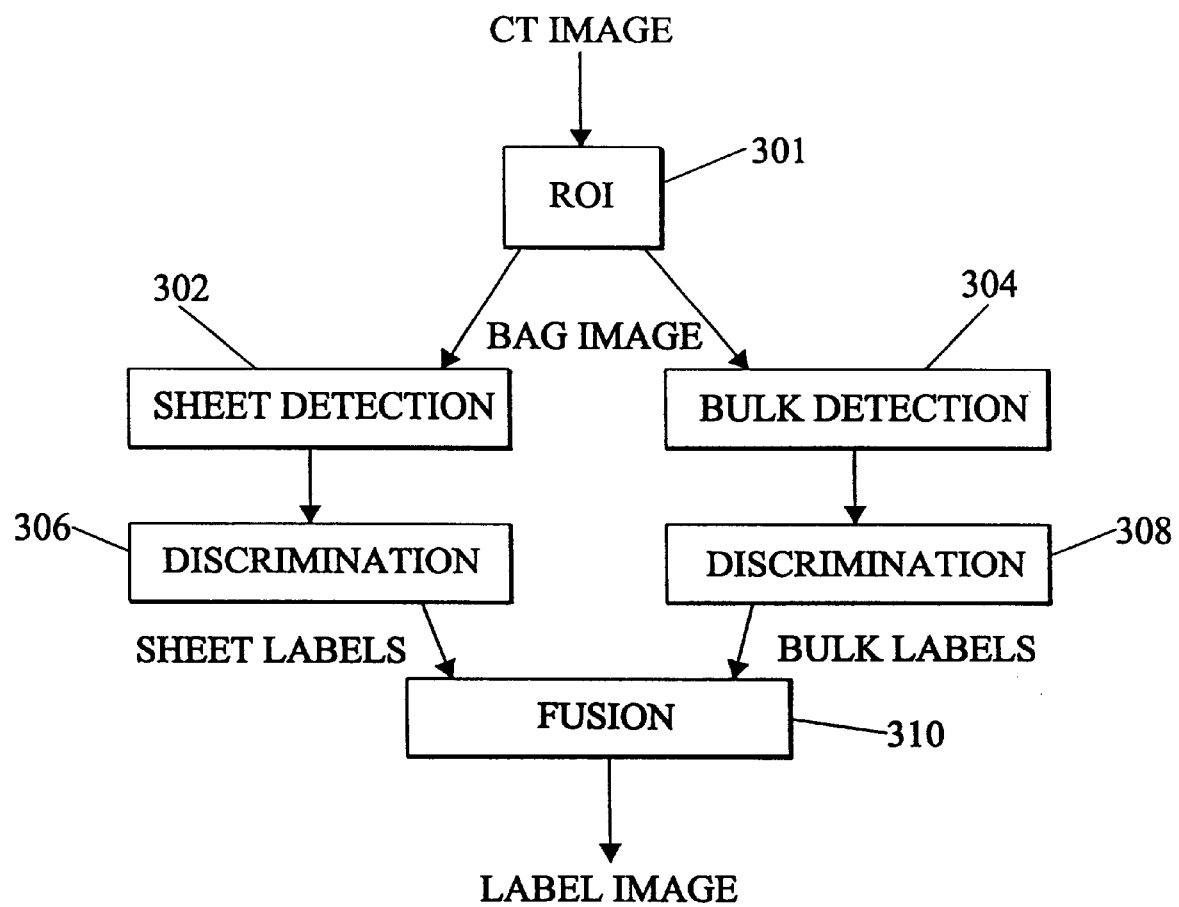
FIG. 5 contains a top-level flow diagram which illustrates the logical flow of one embodiment of the object identification method of the present invention.

FIG. 5 contains a top-level flow diagram which illustrates the logical flow of one embodiment of the object identification method of the invention. In one embodiment, in a first step 301, reconstructed CT image data are received and analyzed to define a region of interest (ROI) or bounding box for the region. This process eliminates voxels outside a bag and therefore reduces the size of the data set considerably. The method can then proceed along parallel paths including a sheet object detection path and a bulk object detection path.

Along the sheet detection path, sheet-shaped objects are detected in the sheet detection step 302. In the discrimination step 306, detected objects are analyzed to determine if they are threats. In one embodiment, this is done by comparing the mass of an object to a mass threshold. The discrimination step 306 produces label image data for the bag, which mark the voxels belonging to each sheet object and identify physical properties of each sheet object (preferably density and mass) and their position in the bag. The label image data for each voxel also include a number identifying the voxel according to an object with which it is identified or identifying the voxel as being background.

Along the bulk detection path, bulk-type objects are detected in the bulk detection step 304. Next, in the discrimination step 308, the detected bulk objects are analyzed to determine if they are threats. The discrimination step 308 produces label image data for the bag, which marks the voxels belonging to each bulk object and identifies physical properties of each bulk object (preferably density and mass) and their position in the bag.

The decision—data fusion step 310 of the method takes the label image data produced by sheet and bulk detection steps and computes a single label image that corresponds to detected explosives. It will be understood that the method described in connection with FIG. 5 can include more than two separate detection paths, depending on the number of types of objects to be identified.

Throughout this application, the term "3-D image" and the symbol $C(i,j,k)$ are used to represent a set of CT slice images. The size of each CT slice is I columns by J rows. The symbol I in $C(i,j,k)$ represents the column index and runs from 0 to I−1. Similarly, the symbol j represents the row index and runs from 0 to J−1. There are K of these slices in a set. The symbol k represents one of these slices and runs from 0 to K−1. The function $C(i,j,k)$ is used to refer to or represent a particular CT density in this set, meaning that it is the CT density value at the ith column and the jth row of the kth slice. The CT densities are represented by positive integers with 0 (Hounsfield units) corresponding to the density of air and 1000 (Hounsfield units) corresponding to the density of water, although if desired other integer values can be used.

The function $C(i,j,k)$ can be considered a 3-D image being I pixels in width, J pixels in height, and K pixels in depth.

Each element in the 3-D image is a voxel. The value $C(i,j,k)$ for a particular voxel denoted by the $(i,j,k)$ triplet is the CT density of the material occupying that voxel.

The size of a voxel is determined by the resolution of the CT equipment. In one embodiment, the scanner has a nominal voxel size of 3.5 mm in width (x), 3.5 mm in height (y), and 3.33 mm in depth (z), which is a relatively small voxel and therefore produces higher resolution when compared to the Eberhard et al. system, although the nominal size can vary depending on several design factors. Using this information and the CT density, it is possible to compute the mass of each voxel in a 3-D image.

CT densities approximately correspond to physical densities of material. Since the CT density of 1000 is made to correspond to the density of water (i.e., 1 gram/cc), in order to find the mass of a given voxel in grams, the CT density value of that voxel is divided by 1000 and multiplied by the volume of the voxel (0.35×0.35×0.333 cc). The method described in this application utilizes this conversion (as the constant $c_0$) to compute the bag mass and the mass of each identified object in the bag.

Figure 6:
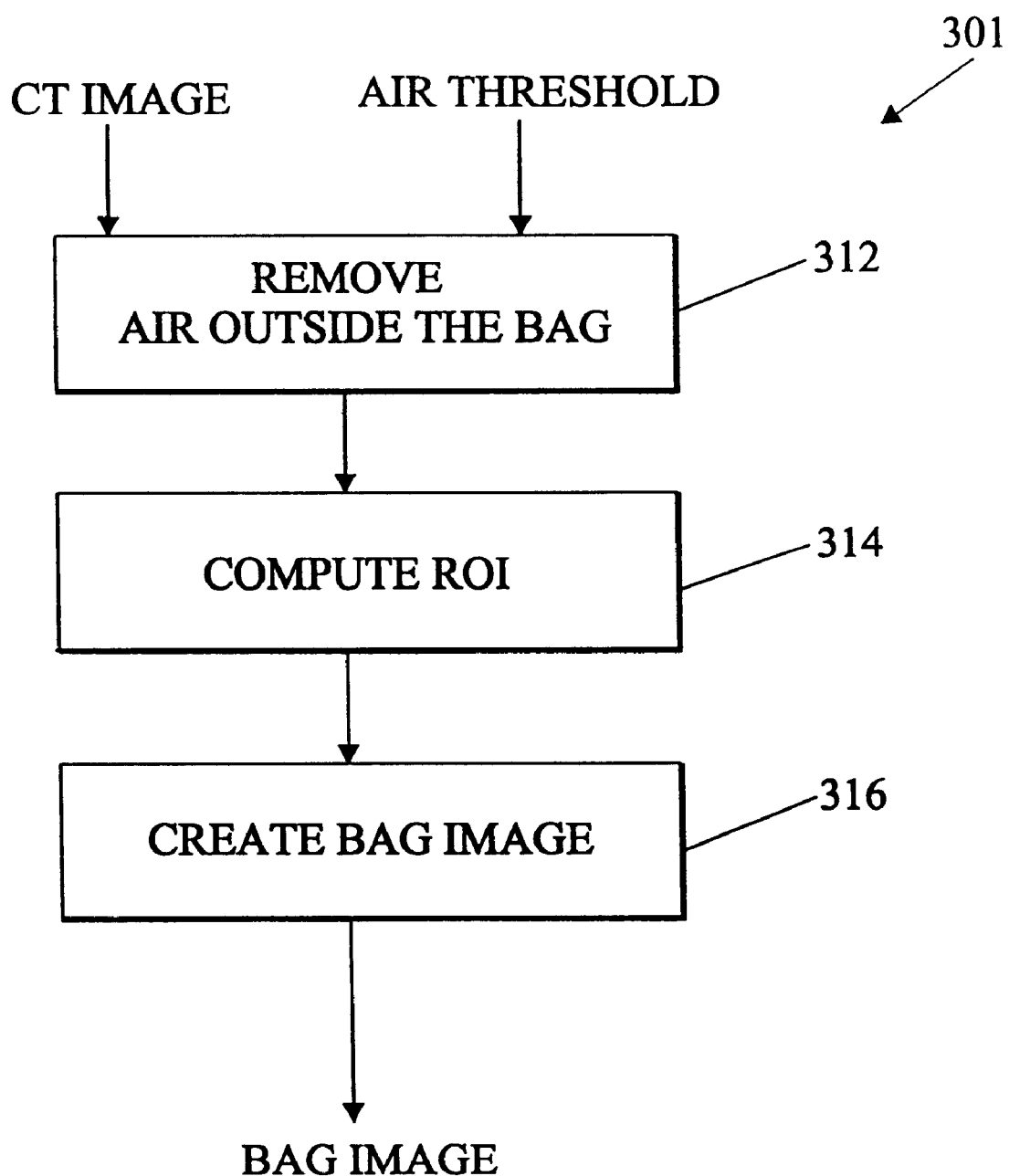
FIG. 6 contains a flow diagram of the logical flow of one embodiment of the region of interest calculation of the present invention.

The main steps in the method of the invention listed above and shown in FIG. 5 will now be described in detail. FIG. 6 contains a flow diagram of the logical flow of one embodiment of the region-of-interest calculation 301 of the present invention. The goal of the region of interest calculation is to eliminate parts of the image that lie outside the bag so that other parts of the process will have less data to analyze and therefore speed up the process and decrease the memory requirements. In one embodiment, a rectangular subset that contains all of the voxels with CT density values in the range of interest is extracted from the original image.

The inputs to the region-of-interest calculation include $C(i,j,k)$, which is the three-dimensional CT-image for a bag. The outputs include $C_{roi}(i,j,k)$, which represents the CT image of a bag region of interest and $(x_{min}, x_{max}, y_{min}, y_{max}, z_{min}, z_{max})$, which are coordinates of the region of the interest box. A parameter used in the calculation is $t_0$ which is the air-to-bag threshold. The method 301 begins by receiving the data representing the 3-D image of a bag, $C(i,j,k)$ and the value for the air threshold $t_0$. Next, in step 312, the voxels identified as containing data representing air are identified, and, in step 314, the coordinates for the region of interest are computed so as to exclude most if not all of those voxels. Steps 312 and 314 proceed as follows so as to define the region of interest:

$x_{min}$=minimum value of I such that at least one $C(i,j,k) \geq t_0$ for any j, k;

$x_{max}$=maximum value of I such that at least one $C(i,j,k) \geq t_0$ for any j, k;

$y_{min}$=minimum value of j such that at least one $C(i,j,k) \geq t_0$ for any I, k;

$y_{max}$=maximum value of j such that at least one $C(i,j,k) \geq t_0$ for any I, k;

$z_{min}$=minimum value of k such that at least one $C(i,j,k) \geq t_0$ for any I, j;

$z_{max}$=maximum value of k such that at least one $C(i,j,k) \geq t_0$ for any I, j.

Figure 7:
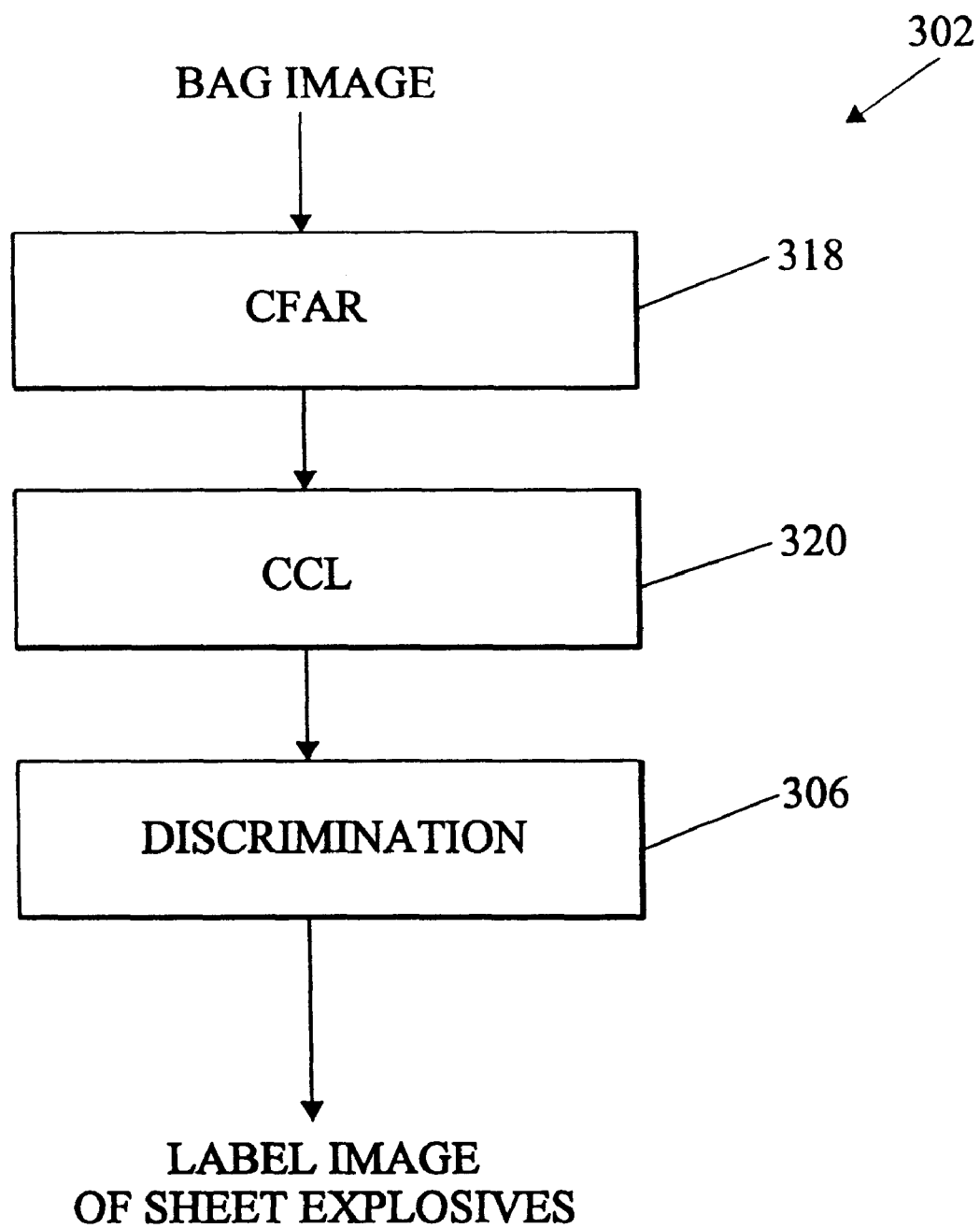
FIG. 7 contains a flow diagram of the logical flow of one embodiment of a sheet detection method in accordance with the present invention.

Next, the image of the region of interest, including the bag, is computed by $C_{roi}(i,j,k)=C(I+x_{min}, j+y_{min}, k+z_{min})$, where $0 \leq I \leq x_{max}-x_{min}$ $0 \leq j \leq y_{max}-y_{min}$ $0 \leq K \leq z_{max}-z_{min}$ FIG. 7 is a flow diagram which illustrates the logical flow of one embodiment of a sheet detection method in accordance with the present invention. Sheet explosives are characterized as being much thinner in one dimension (height, width, or depth) than in the other two. This dimension is referred to as the thickness of a sheet explosive. One sheet explosive detection method described herein is tunable to the sheet thickness and uses a constant false alarm rate (CFAR) method. Two-dimensional approaches to CFAR are described in, for example, Kreiten, et al., "Discriminating Targets from Clutter," Lincoln Lab Journal, Vol. 6, No. 1, 1993; Novak, et al., "Effects of Polarization and Resolution on the Performance of a SAR Automatic Target Recognition System," Lincoln Lab Journal, Vol. 6, No. 1, 1993; and Frosgate, et al., "Multiscale Segmentation and Anomaly Enhancement of SAR Imagery," IEEE Trans. on Imag. Proc., Vol. 6, No. 1, 1997; all of which are incorporated herein by reference. Under the three-dimensional CFAR approach of the invention, a CFAR sheet voxel analysis step 318, as described below in detail, is performed on the CT image data for the region of interest to identify which voxels are associated with sheet objects. Next, a connected components labeling (CCL) method can be applied in step 320 to sheet voxels to connect them within individual objects. In step 306, the objects are classified such as by mass discrimination.

Figure 8A:
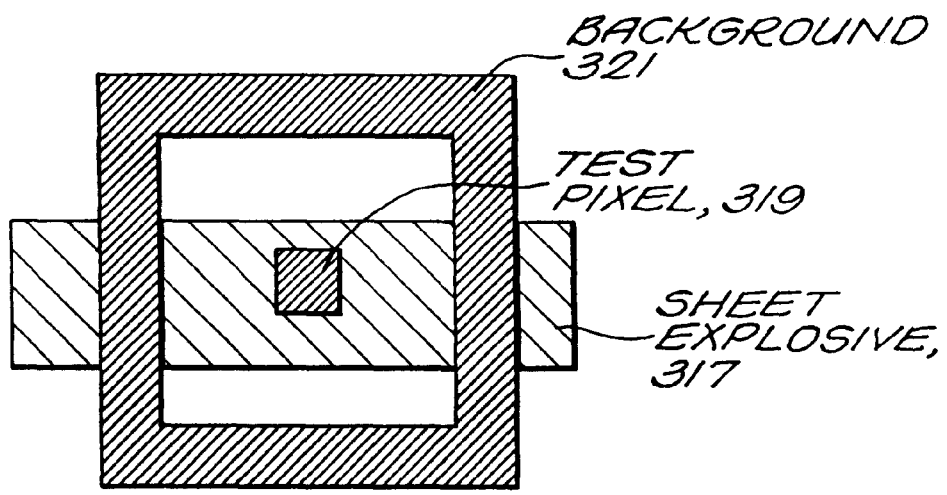
FIGS. 8A and 8B schematically illustrate the sheet object detection method of FIG. 7.
Figure 8B:
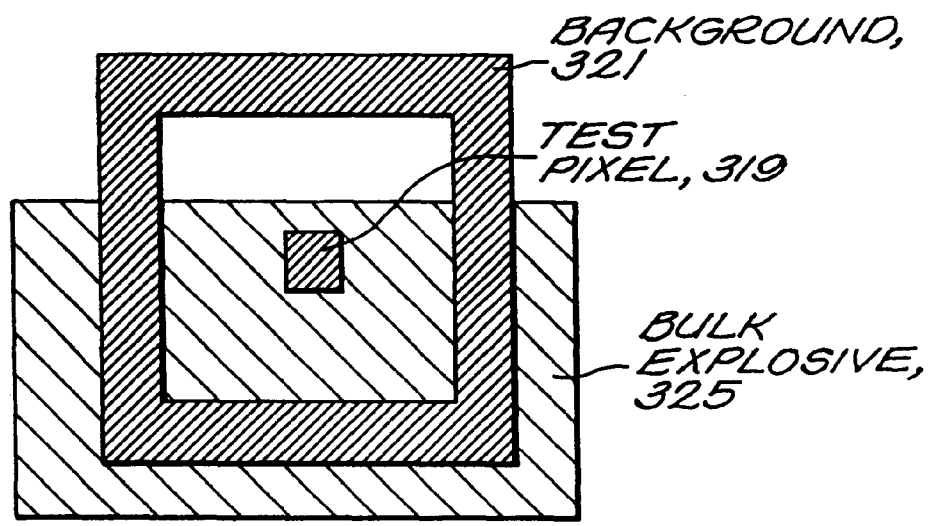

Under the CFAR method of the invention, each voxel in the bag is examined to determine whether it is part of a sheet explosive. To be part of a sheet explosive a voxel should have a density value within a certain range of CT density values and should be statistically distant from its background. In one embodiment, the background is defined as the voxels on the surface of a cube of size comparable to the sheet thickness that is centered around the test voxel as shown in FIGS. 8A and 8B, which are schematic diagrams of the preferred CFAR method of the present invention. FIG. 8A shows in two dimensions the background cube 321 including a test voxel 319 being applied to CT data voxels that include a sheet object 317. The mean and standard deviation of the background voxels around the test voxel are computed. The value of the test voxel is compared against the mean and standard deviation of the background. If the statistical distance of the test voxel to its background is larger than a predetermined threshold, then the test voxel is said to belong to a sheet explosive.

In one alternative embodiment, all of the voxels on the surfaces of the cube are not used to compute the mean and standard deviation. To save processing time, the voxels at a surface can be sampled, and only the sampled voxels can be used in the computation of the mean and standard deviation. In one embodiment, only every other voxel is sampled, resulting in savings of half the processing time required to generate the mean and standard deviation.

In another alternative embodiment, three separate two-dimensional CFAR calculations can be performed in the three orthogonal Cartesian planes, x-y, x-z, y-z. A voxel mean and standard deviation of the background are computed for each plane, the background being defined as the voxels on the perimeters of a square in the respective plane. Then, statistical distances are computed for each plane and are compared to a predetermined threshold. Different coordinate planes may have different thresholds. The number of planes in which the threshold is exceeded is used to determine whether the voxel is a sheet voxel. For example, if one or more thresholds are exceeded, then it can be concluded that the voxel is a sheet voxel. In another embodiment, the voxel is labeled a sheet voxel if two or more thresholds are exceeded.

In all cases of the CFAR method of the invention, an upper threshold in addition to or instead of the lower threshold can be employed. This will eliminate sheet-shaped objects which have very high contrast with background. An example of such a sheet would be the outer surface of the bag.

As shown in FIG. 8B, for bulk object 325, the background voxels cover more of the object itself. Hence, the background becomes statistically close to the test voxel which is chosen to be in the test object. Therefore, the CFAR distance is large for thin sheet-like objects and small for thick bulk-like objects. This property is used to detect all voxels that belong to sheet-like objects and eliminate all voxels that belong to bulk objects in the bag.

In accordance with the invention, a three-dimensional CFAR method is applied to the CT data to detect sheet objects. In developing the three-dimensional CFAR of the invention, selecting the size of the void region between the target voxel and the background voxels was considered. A standard two-dimensional prior art CFAR process, such as the processes described in the literature mentioned above, requires that the background samples be taken from an area that does not include any part of the target. In the application of the present invention in which sheet objects are detected, in the case of a sheet, only one dimension of the target object is known and the orientation of that dimension is not known. So, if the prior art CFAR approach were applied, it would be difficult to sample the background as the prior art CFAR process requires. In the implementation of the invention, parts of the target object are sampled as background also. In the present invention, including some of the target samples in the background samples changes the mean and the standard deviation of the background samples. But the change is different for different target coverage of the CFAR sampling region. This fact helps the invention distinguish between sheet-like objects and bulk objects. This difference between sheet coverage and bulk coverage is illustrated in FIGS. 8A and 8B.

After deciding which voxels to consider as sheets, the CCL analysis 320 is performed on the sheet voxels to combine the voxels into a sheet object. The mass of each connected component thus obtained is compared against a predetermined mass threshold to decide the presence of a sheet explosive.

Hence, the present invention uses a CFAR approach that is extended to three dimensions and is substantially modified and improved over the two-dimensional techniques described in the literature. In the present invention, the modified CFAR is used as one step in a process to identify a threat. The modified CFAR of the invention first classifies individual voxels according to whether they are part of sheet objects. Next, the process of the invention continues with additional steps such as CCL to combine the voxels into objects and discrimination steps to determine whether the objects pose threats. In contrast, the prior two-dimensional CFAR approaches were used as stand-alone detection algorithms whose outputs consisted of a final classification of an object based on two-dimensional CFAR analysis of a pixel in the object.

As noted above, the goal of the sheet explosive detection method is to detect sheet-like objects. A separate sheet explosive detection step is used to solve the problem of sheets being inadvertently removed from the data during morphology steps such as erosion performed during the bulk detection process. The inputs to the sheet detection method include $C_{roi}(i,j,k)$, which is the 3-D image of the region of interest (size $I_{roi} \times J_{roi} \times K_{roi}$). The outputs of sheet explosive detection include the following:

$L_s(i,j,k)$, Label image for sheet explosives (same size as $C_{roi}$);

$N_s$, Number of detected sheet explosives;

$\rho_n$, Density of each detected object;

$M_n$, Mass of each detected object; and $(x^n_{min}, x^n_{max}, y^n_{min}, y^n_{max}, z^n_{min}, z^n_{max})$ Bounding box for each detected object.

A bounding box as used in connection with this and other aspects of the invention is defined as the smallest rectangular region which contains the object that it bounds. The parameters for sheet detection include the following:

$(\rho^s_{min}, \rho^s_{max})$, CT-density range of interest for sheets;

$g$, Size of the CFAR cube around the test pixel in voxels;

$t_1$, CFAR decision threshold;

$\Delta_s$, CCL threshold;

$c_s$, CCL connectivity type (any combination of "face", "edge", or "vertex");

$m_s$, Mass threshold for sheet explosive detection; and $c_0$, CT density-to-mass conversion factor.

In one embodiment, the steps in the sheet explosive detection method include the following:

1. Start with the 3-D image of the ROI, $C_{roi}(i,j,k)$.

2. Pad the image with $g$ layers of voxel values having some preset background value, e.g., zero, on each side to create a padded image, $P(i,j,k)$, size $(I_{roi}+2g) \times (J_{roi}+2g) \times (K_{roi}+2g)$, $$P(i, j, k) = \begin{cases} C_{roi}(i-g, j-g, k-g) & g \leq i < (I+g) \\ & g \leq j < (J+g) \\ & g \leq k < (K+g) \\ 0 & \text{otherwise} \end{cases} \quad (1)$$

3. Raster scan the padded image and find the voxels, $\{v_0=(i_0,j_0,k_0), v_1=(i_1,j_1,k_1), \ldots v_n \ldots\}$, with a CT density between $\rho^s_{min}$ and $\rho^s_{max}$. A shorthand notation $v_n$ is used to denote a voxel, $0 \leq n < (I_{roi}+2g)(J_{roi}+2g)(K_{roi}+2g)$.

4. For each voxel $v_n=(i,j,k)$ the surface of the CFAR cube, $S_n$ is defined as the surface voxels $v_{n'}=(i',j',k')$ of the $(2g+1) \times (2g+1) \times (2g+1)$ cube centered at $v_n$:

$$(i', j', k') \in S_n \text{ if } \begin{cases} j-g \leq j' \leq j+g, k-g \leq k' \leq k+g, & i' = i \pm g \\ i-g \leq i' \leq i+g, k-g \leq k' \leq k+g, & j' = j \pm g \\ i-g \leq i' \leq i+g, j-g \leq j' \leq j+g, & k' = k \pm g \end{cases} \quad (2)$$

The number of voxels in $S_n$ (the surface area of the cube) is equal to $A_{S_n} = 24 g^2 + 2$ 5. On the surface $S_n$ of the CFAR cube centered around each $v_n$, compute the mean, $\mu_n$, $$\mu_n = \frac{1}{A_{S_n}} \sum_{v_{n'} \in S_n} P(v_{n'}) \quad (3)$$

6. On the same surface compute the standard deviation, $\sigma_n$, $$\sigma_n = \sqrt{\frac{1}{A_{S_n}} \sum_{v_{n'} \in S_n} P^2(v_{n'}) - \mu_n^2} \quad (4)$$

7. Compute the distance, $d$, of the voxel $v_n$, to the background given by $\mu_n$ and $\sigma_n$, $$d_n = \frac{P(v_n) - \mu_n}{\sigma_n} \quad (6)$$

8. Create a CFAR image $CFAR(i,j,k)$, same size as input image $C_{roi}(i,j,k)$ (not zero padded), consisting only of the voxels whose distance, $d_n$, exceeds the threshold $t_1$, $$CFAR(i-g, j-g, k-g) = \begin{cases} P(i, j, k) & d_n \geq t_1 \\ 0 & \text{otherwise} \end{cases} \quad (6)$$

9. Perform connected component labeling (CCL) using the CCL parameters, $\Delta_s$ and $c_s$, on the CFAR image, CFAR $(i,j,k)$, to produce a label image $L_s(i,j,k)$ and bounding boxes, $(x^n_{min}, x^n_{max}, y^n_{min}, y^n_{max}, z^n_{min}, z^n_{max})$, $$L_s(i, j, k) = \begin{cases} \text{object label } 0 < l \leq N_s & \text{for } CCL \text{ objects} \\ 0 & \text{otherwise} \end{cases} \quad (7)$$

10. For each object $l=1, \ldots N_s$ the mass $M_l$ is computed during the CCL.

$$M_l = c_0 \sum_{i,j,k} CFAR(i, j, k) h(L_s(i, j, k), l) \quad (8)$$

where the selector function, $h(x,l)$, is defined as $$h(x, l) = \begin{cases} 1 & x = l \\ 0 & \text{otherwise} \end{cases} \quad (9)$$

11. Eliminate all objects whose mass, $M_l$, is below the given mass threshold, $m_s$.

$L_s(v_n) = 0$ if $M_{L_s(v_n)} < M_S$ \quad (10)

12. Renumber the remaining objects using consecutive positive integer labels and update the label image. Set $N_S$ equal to the number of remaining objects.

It should be noted that, with respect to the sheet detection method, the variance $\sigma^2_n$ can be used in place of the standard deviation $\sigma_n$ in step 5. This can increase the execution speed of the implementation. Also, shapes other than a cube could be used to define a CFAR surface. In addition, thick sheet explosives can be detected by the bulk path of the method of the invention. Therefore, in one embodiment, the thickness of sheets to be detected can be set to be slightly thicker than the thinnest sheet that can be detected by bulk detection.

In another aspect of the invention, sheet objects can be detected in the density data by using a morphology approach analogous to the morphological CCL applied ir bulk object detection. Under this morphological sheet detection approach, all objects in the data are eroded a predetermined number of times such that all thin sheet shaped objects are eliminated from the data. The number of erosions performed is based on the number of erosions needed to eliminate sheet objects from the data, which is related to the thickness of a sheet. Each erosion can remove one layer of surface voxels. Therefore, the number of erosions is related to the expected thickness of a sheet and the size of a voxel. After all of the erosion steps are performed, the objects remaining in the data are assumed to be bulk objects. The data associated with these objects are then eliminated from further processing. The original data, with the bulk objects removed, are then analyzed to label the sheet objects. The remaining voxels are analyzed one at a time such as by the CCL process to combine voxels into sheet objects and then label the sheet objects. Next, discrimination is performed on the sheet objects to classify them as threats or non-threats, such as by comparing the objects mass to a predetermined mass threshold. Sheets with masses above the threshold can be classified as threats.

It should be noted that other sheet detection approaches such as high-pass filtering can be used with the various aspects of the invention to detect sheets. Also, the connection process, e.g., CCL, can be applied either to the binary data produced by sheet detection or to the product of the binary data and the associated voxel density data.

The bulk object detection process of the invention searches the bag image for clusters of voxels in the density range of interest, can label them as bulk objects, and can use mass-dependent density thresholds to determine if an object is a threat.

In one embodiment, the bulk detection process uses the CCL method to identify objects in the three-dimensional bag image. One of the main problems in using CCL is compound objects, i.e., two or more physical objects in close proximity growing together into a single object in the bag image due to the finite resolution of the system causing partial volume effects. To solve this problem, in one embodiment of the invention, the image is preprocessed before the application of CCL to split compound objects. This preprocessing can be done using an erosion operator as described below in detail, which effectively removes the surface layer of voxels from objects to prevent CCL from growing multiple objects together. To balance the effects of erosion on object size, a dilation operation as described below in detail is applied after an eroded image is segmented into objects by CCL. This operation adds the surface voxels back to the objects after the objects have been determined to be separate objects.

In accordance with one aspect of the invention, the bulk detection method uses one or more separate density ranges, one for each type of bulk material of interest having density values falling within the range. In one embodiment, there are two separate density ranges used in the bulk detection. The density ranges are chosen according to the objects sought to be identified. In one particular embodiment, one of the ranges covers a first specific type of explosive (referred to herein as "type A"); the other one includes all solid bulk explosives exclusive of type A. Since explosive types and typical false alarms in these two density ranges differ, separate detection paths with different erosions and dilations can be used to optimize performance for each density range.

In one embodiment, the detection process for a given density range has the following steps:

1. Perform at least one erosion to remove surface voxels.
2. Use CCL to segment the image into separate objects.
3. Restore surface voxels to the objects using the dilation operator.
4. Compute object properties.
5. Use mass thresholds to discriminate between explosives and non-threat objects.

Once the bag image is segmented into objects, such properties as mass, mean density, eroded mass, and eroded mean density are computed for each object. Density dependent mass thresholds are used to discriminate between threat and non-threat objects. The number of potential explosive objects, their properties and their coordinates in the bag image are returned by the bulk detection process.

The inputs to the bulk detection process include $C(i,j,k)$, the 3-D CT image of a bag. The outputs include the following:

$N_b$, Number of detected bulk objects;

$L_b(i,j,k)$, Label image, same size as $C(i,j,k)$;

$(x^{min}_n, y^{min}_n, z^{min}_n), (x^{max}_n, y^{max}_n, z^{max}_n)$, Bounding box coordinates for each object;

$V_n$, Number of voxels in each object;

$M_n$, Mass of each object;

$V^e_n$, Eroded number of voxels in each object; and $M^e_n$, Eroded mass of each object.

Parameters used by the process include:

$(\rho^p_{min}, \rho^p_{max})$, Density range for type A explosive;

$(\rho^{pe}_{min}, \rho^{pe}_{max})$, Erosion density range for type A explosives;

$(\rho^b_{min}, \rho^b_{max})$, Density range for bulk explosives;

$(\rho^{be}_{min}, \rho^{be}_{max})$, Erosion density range for bulk explosives;

$(\rho^{bd}_{min}, \rho^{bd}_{max})$, Dilation density range for bulk explosives;

$(\rho^{bm}_{min}, \rho^{bm}_{max})$, Density range for bulk explosives object merging;

$\Delta_m$, Maximum eroded density difference between objects for bulk explosives object merging;

$e_p$, Number of erosions in the type A density range;

$e_b$, Number of erosions in the bulk density range;

$n_p$, Minimum number of neighboring voxels in the type A erosion density range required to keep a type A voxel;

$n_b$, Minimum number of neighboring voxels in the bulk erosion density range required to keep a bulk voxel;

$\Delta_b$, Maximum density difference for connecting voxels in CCL;

$c_b$, Connectivity type for CCL;

$\rho_t$, Density threshold between low density and high density bulk explosives;

$m_p$, Mass threshold for cylindrical objects containing type A explosives;

$m_l$, Mass threshold for low density bulk explosives;

$m_h$, Mass threshold for high density bulk explosives;

$V_{min}$, Minimum number of voxels required to keep an object after the image segmentation step; and $c_v$, Voxel volume.

Figure 9:
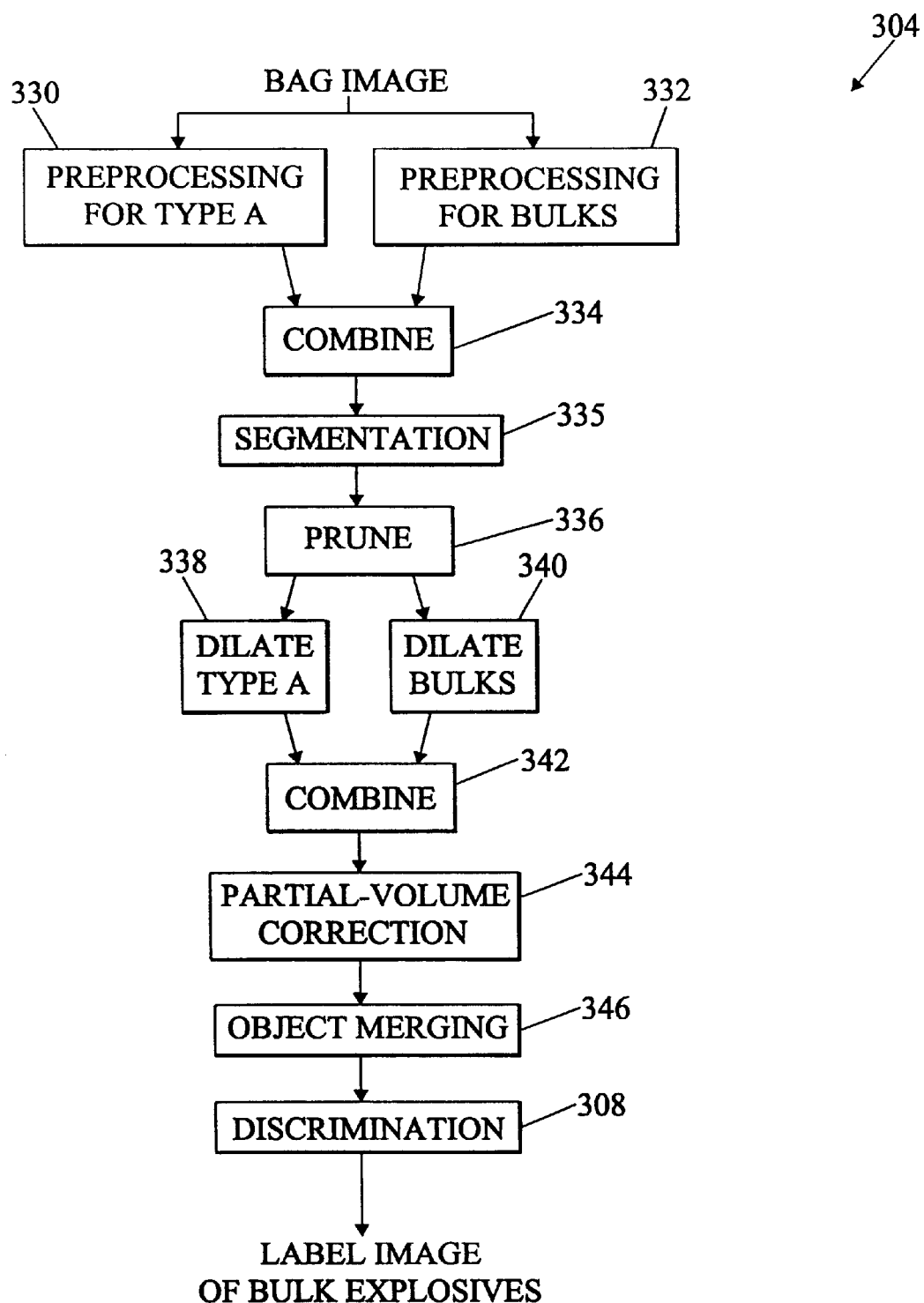
FIG. 9 contains a flow diagram of the logical flow of one embodiment of a bulk object detection method in accordance with the present invention.

FIG. 9 is a schematic flow diagram which illustrates the logical flow of one embodiment of the bulk object detection method of the invention. The bag image voxels are received for preprocessing steps 330 and 332. In the embodiment shown in FIG. 9, the preprocessing steps including object erosion are performed separately in parallel. Specifically, preprocessing for type A materials is performed in step 330 and preprocessing for bulks is performed in step 332. It will be understood that these preprocessing steps need not be performed in separate parallel steps.

The erosion operator is applied recursively image-by-image to the original CT image $e_p$ times for the type A erosion density range $(\rho^{pe}_{min}, \rho^{pe}_{max})$ in step 330, and/or $e_b$ times for the bulk erosion density range ($\rho^{be}_{min}, \rho^{be}_{max}$) in step 332. The first iteration is the original CT image, i.e., $C^0(i,j,k)=C(i,j,k)$. Further iterations are created by applying the erosion operator to each voxel. For each voxel (i,j,k) the erosion operator performs the following steps.

1. Check if the voxel belongs to one of the erosion density ranges of interest, set its CT value to zero and go to the next voxel if it does not:

$$C^{n+1}(i,j,k) = \begin{cases} C^n(i,j,k) & \text{for } \rho^{be}_{min} \leq C^n(i,j,k) \leq \rho^{be}_{max} \\ C^n(i,j,k) & \text{for } \rho^{pe}_{min} \leq C^n(i,j,k) \leq \rho^{pe}_{max} \\ 0 & \text{otherwise} \end{cases} \quad (11)$$

2. Examine the 3×3×3 neighborhood of the current voxel (i,j,k). Count the number N of voxels ($i^1,j^1,k^1$) with CT values $C(i^1,j^1,k^1)$ in the same density range as the current voxel (either type A or bulk).

3. If the count is below the threshold, either $n_p$ or $n_b$, set $C^{n+1}(i,j,k)$ equal to zero, otherwise keep the current voxel. The thresholds are different for bulks and type A materials:

$$C^{n+1}(i,j,k) = \begin{cases} C^n(i,j,k) & \text{if } N \geq n_b \text{ and } \rho^{be}_{min} \leq C^n(i,j,k) \leq \rho^{be}_{max} \\ C^n(i,j,k) & \text{if } N \geq n_p \text{ and } \rho^{pe}_{min} \leq C^n(i,j,k) \leq \rho^{pe}_{max} \\ 0 & \text{otherwise} \end{cases} \quad (12)$$

Standard morphological erosion keeps a voxel only if the voxel neighborhood fits a certain pattern mask. Typically, only voxels with all 27 neighbors in the range of interest are kept. Standard erosion is described in, for example, Serra, J., *Image Analysis and Mathematical Morphology*, Academic Press, London, 1982. It should be noted that the erosion operator employed in the morphological CCL of the invention can be the voting or counting operator described above. Other erosion operators, such as the one described by Serra, can also be used.

In the process of the invention, the purpose of the erosion operation is to separate objects that are in close proximity to each other and, as a result, can be merged together by standard CCL. In the present invention, the outside surfaces of objects are eroded. On the other hand, some objects have internal holes (such as thin cylindrical axial cavities in cylindrical stick-like objects) or voxels that fall outside the density range of interest due to noise or artifacts in the image. Eroding these internal surfaces can split the objects into several parts, or it can eliminate the object completely in the case of thin objects with axial cavities.

The outer surfaces of objects are usually convex, while the surfaces of internal cavities are usually concave. Therefore, voxels on outside surfaces are likely to have fewer object voxels in the 3×3×3 neighborhood than voxels on the inside surfaces. The count threshold can be used to selectively erode only the outer surfaces of objects while preserving the object interior.

The results of the two preprocessing steps 330 and 332 are combined in the optional combine step 334. In the embodiment shown in which separate paths are used for preprocessing, each preprocessing step 330 and 332 generates a unique set of preprocessed data from the original bag image data. In the combine step 334, these individual sets of data are combined into a single set of preprocessed data.

In the segmentation step 335, CCL can be used to identify and label objects in the eroded CT image data. Neighboring voxels in the same density range, either bulk ($\rho^b_{min}, \rho^b_{max}$) or type A ($\rho^p_{min}, \rho^p_{max}$), are connected and assigned an object label. Neighboring voxels are defined as a combination of "face", "edge", or "vertex" neighbors, determined by the CCL connectivity parameter $c_b$.

A single run of the CCL process can find objects in both density ranges, as long as the gap between them is greater than the maximum density difference for connecting voxels in CCL, $\rho^b_{min} - \rho^p_{max} > \Delta_b$. Using only a single CCL run to compare voxels to multiple density ranges is much more efficient and less time consuming than performing a separate CCL run for each range, since CCL in general utilizes a large amount of processing resources. If the threshold difference $\Delta_b$ is selected to be smaller that the gap between the density ranges, then the chance of mislabeling a voxel of a material of one of the ranges as belonging to another range is eliminated, thus allowing the process to be run for multiple ranges simultaneously. It will be understood that this approach can be extended to any number of ranges separated by gaps at least as large as the threshold $\Delta_b$.

The label image is created, where each voxel (i,j,k) is assigned a value $$L_b(i,j,k) = \begin{cases} 0, & \text{voxel is not in either one of the density ranges;} \\ 1 \leq n \leq N_b, & \text{voxel belongs to nth object;} \end{cases} \quad (13)$$

where $N_b$ is the total number of objects found in a bag image. Eroded number of voxels, $V^e_n$, and eroded mass, $M^e_n$, are computed for each object n at the relabeling pass of the CCL.

In the pruning step 336, objects consisting of only a few voxels ($V^e_n < V_{min}$) are discarded and corresponding voxels in the label image, $L_b(i,j,k)$, are set to zero. The total number of objects $N_b$ is decreased, remaining objects are renumbered using consecutive labels, and the label image is updated with new object labels.

A type A dilation step 338 and/or a bulk dilation step 330 can then be performed. As in the preprocessing erosion steps 330 and 332, the dilation steps 338 and 330 can be performed in separate parallel paths. In dilation, a layer of voxels is added to remaining objects in order to restore the mass and volume lost in erosion. For each labeled voxel ($l=L_b(i,j,k)>0$), the eroded density of the object labeled l that contains the current voxel is given by $$D_l = \frac{M^e_l}{c_v V^e_l} \quad (14)$$

where $M^e_l$ and $V^e_l$ are computed during CCL. This density is used to determine if the voxel is part of a bulk explosive object or a type A object. The CT density $C(i^1,j^1,k^1)$ of all unlabeled voxels ($L_b(i^1,j^1,k^1)=0$) in the 3×3×3 neighborhood of the current voxel (i,j,k) is examined. If the density is within the dilation density range corresponding to the explosive class (bulk or type A) of the current object, $$C(i',j',k') \in \begin{cases} (\rho^{pe}_{min}, \rho^{pe}_{max}), & \text{if } \rho^p_{min} \leq D_l < \rho^p_{max} \\ (\rho^{bd}_{min}, \rho^{bd}_{max}), & \text{if } \rho^b_{min} \leq D_l \leq \rho^b_{max} \end{cases} \quad (15)$$

then the voxel ($i^1,j^1,k^1$) is assigned the same label as voxel (i,j,k), $$L_b(i^1,j^1,k^1)=l, \quad (16)$$

and the total number of voxels, $V_1$, and the total mass, $M_1$ are incremented. Dilation can be performed recursively $e_p$ times for the type A density range, and $e_b$ times for the bulk density range.

A second combine step 342 can then be performed on the dilated data. In the embodiment shown in which separate paths are used for type A and bulk dilation, each dilation step 338 and 330 generates a unique set of dilated data from the eroded, segmented and pruned bag image data. In the combine step 342, these individual sets of data are combined into a single set of dilated data.

A partial volume correction step 344 can then be performed. The mass of each object is enhanced by replacing the measured CT density of voxels added by dilation with the average density of the object.

$$M_n = M_n^e + M_n V_n - \frac{V_n^e}{V_n} \quad (17)$$

Partial volume correction 344 is described below in detail.

An object merging step 346 can then be performed. If bounding boxes of objects n and m overlap and their eroded densities are close, i.e., $$|D_n - D_m| \leq \Delta_m, \quad (18)$$

then the objects can be merged into a new single object with mass $M = M_n + M_m$ and number of voxels $V = V_n + V_m$. The label image $L_b(i,j,k)$ is updated so that merged objects have the same label. Use of this merging in the analysis of stick-shaped object detection is described below in detail.

Discrimination 308 can then be performed. For each object n, $1 \leq n \leq N_b$, the decision is made whether this object is a potential threat based on the object mass and eroded density:

$$\text{object is a threat if} \begin{cases} M_n \geq m_p & \text{for } \rho_{\min}^p \leq D_n \leq \rho_{\max}^p \\ M_n \geq m_l & \text{for } \rho_{\min}^b < D_n < \rho_t \\ M_n \geq m_h & \text{for } \rho_t \leq D_n \leq \rho_{\max}^b \end{cases} \quad (19)$$

This density dependent mass thresholding is described below in detail.

The connected component labeling (CCL) approach used in the invention is used to detect objects with density values in the predefined range of interest in the 3D image. CCL is a process which determines if a voxel belongs to a particular object. An object is defined as a topologically connected (a combination of "face", "edge", and "vertex" connectivity determined by the parameter c) set of voxels with voxel CT density values within a range of interest from $\rho_1$ to $\rho_h$ and with the difference in voxel values between neighboring voxels within a delta value $\Delta$.

The 3D image is represented by the C(i,j,k) array. Index $0 \leq k < K$ is the slice number (index along the Z axis), where the value of K is determined by the length of the bag. Index $0 \leq j < J$ is the row number (index along the Y axis), where, in one embodiment, J=117 or 158 depending on the bag shape (oblong or square). Index $0 \leq i < I$ is the column number (index along the X axis), where, in one embodiment, I=214 or 158 depending on the bag shape (oblong or square).

An array L(i,j,k) of the same size as C(i,j,k) is used to label voxels as either background (labeled by L(i,j,k)=0) or as belonging to an object number n>0 (labeled by L(i,j.k)= n). The label equivalency array, l(i), is used by the CCL algorithm to assign a unique label to each object. This array must be initialized as l(i)=i, $0 \leq i \leq L_{max}$, where the constant $L_{max}$ is determined by the maximum number of separate objects that can be found in a bag.

Three different topological definitions of neighboring voxels $(i_n, j_n, k_n)$ ($|i-i_n| \leq 1, |j-j_n| \leq 1, |k-k_n| \leq 1$) being connected to the current voxel (i,j,k) can be used in the 3D CCL process:

1. Voxels (i,j,k) and $(i_n, j_n, k_n)$ share a common face, $|i-i_n| + |j-j_n| + |k-k_n| = 1$.
2. Voxels (i,j,k) and $(i_n, j_n, k_n)$ share a common edge, $|i-i_n| + |j-j_n| + |k-k_n| = 2$.
3. Voxels (i,j,k) and $(i_n, j_n, k_n)$ share a common vertex, $|i-i_n| + |j-j_n| + |k-k_n| = 3$.

A combination of these connectivity types can be specified as an input parameter for the CCL process. It should be noted that when the current voxel (i,j,k) is on the surface of the bag image (either i,j, or k equal to 0 or their respective maximum values), not all possible neighboring voxels exist.

FIG. 10 contains pseudocode describing one embodiment of the CCL method of the invention. The first step of the CCL method is a raster scan through the image data. It assigns preliminary labels to the voxels. If the current voxel is within the density range of interest, then it is tested against its neighboring voxels. If the neighboring voxel value is within the $\Delta$ range of the value of the current voxel, these two voxels are part of the same object. Since the first pass is performed sequentially, it is possible to assign different label numbers to different parts of the same object. When the merger point is encountered, the equivalency of the labels is noted in the l(i) array. The lowest available equivalent label is used to avoid circular references.

The second step of the method is to resolve all label equivalencies in the l(i) array, count the number of separate objects $N_b$ and assign each label an equivalent value ranging from 1 to $N_b$. The third step is to relabel the voxels with the equivalent label values, L(i,j,k)=l(L(i,j,k)) for all (i,j,k). During this pass, necessary information about each object can be accumulated, such as the bounding box indices and the total mass of the object.

Figure 11:
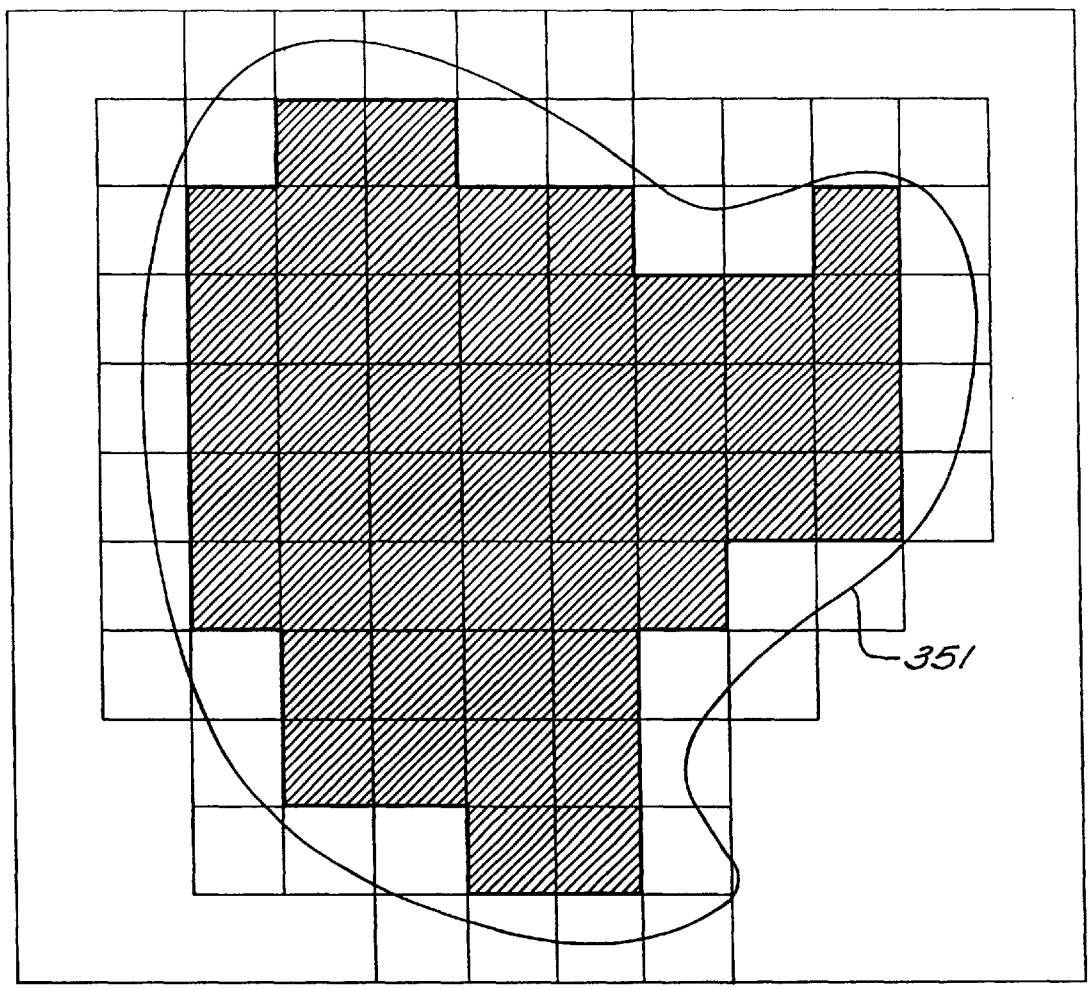
FIG. 11 is a schematic illustration of the partial volume effect.

Partial volume correction or mass enhancement of an object addresses the problem of density degradation of the surface voxels of the scanned objects. The CT value of a given voxel represents the average density of the object within that voxel. As a result, an accurate measure of the object density can only be obtained if the voxel is totally contained in the object. On the other hand, if the voxel is partially occupied by the object, its density will be degraded based on the occupied portion of the voxel. FIG. 11 shows the partial volume effect on a scanned object 351. In FIG. 11 non-shaded voxels (squares) are affected by the partial volume effect. The partial volume correction of the invention is based on substituting the CT values of the surface voxels of the scanned object using its mean CT density or the mean of its eroded CT density.

Because of the partial volume effect, the actual density and mass of a scanned object are larger than their measured values. The difference in values depends on the shape of the object; more specifically, it depends on the surface-to-volume ratio of the scanned object. An object with a large surface-to-volume ratio, such as a sheet or a cylinder of small diameter, will be more affected than an object with small surface to volume ratio, such as bulk object or a cylinder of large diameter. The measured CT density of a scanned object is defined as the averaged density of all its voxels:

$$\overline{\rho} = \frac{\sum_{v \in O} \rho_v}{N} \quad (20)$$

where $\rho_v$ is the CT density of the vth voxel of the object, O is the scanned object, and V is the number of voxels of the scanned object as found by CCL. The mass of the object is then:

$$\bar{M} = NCV\bar{\rho} = \sum_{v \in O} CV\rho v \quad (21)$$

where V is the volume of a voxel and C is a mass conversion constant.

The object voxels can be divided into surface and core voxels. Surface voxels are voxels having less than 26 neighbors of the scanned object voxels. A more accurate density measure can be computed using only the core voxels of the scanned object. The new density is known as the eroded density:

$$\bar{\rho}_e = \frac{\sum_{v \in C_O} \rho_v}{N_e} \quad (22)$$

where $C_O$ is the core of the scanned object, and $N_e$ is the number of eroded voxels of the scanned object. $N_s$, the number of surface voxels, is given by $N-N_e$. Let $S_O$ be the set of surface voxels, the mass can be written as follows:

$$\bar{M} = \sum_{v \in C_O} CV\rho_v + \sum_{v \in S_O} CV\rho_v \quad (23)$$

The extent of mass reduction by the partial volume effect is determined by the second term of the right hand side of Equation 23, since $\rho_v$ will be most affected at the object surface. One way of correcting that is to use the averaged density or the eroded density for replacing $\rho_v$ in the second term of the right hand side of Equation 23. The corrected mass can be computed using one of the following equations:

$$\hat{M} = \sum_{v \in C_O} CV\rho_v + N_s CV\bar{\rho} \quad (24)$$

$$\hat{M} = \sum_{v \in C_O} CV\rho_v + N_s CV\bar{\rho}_e \quad (25)$$

The eroded or the averaged density can be chosen to replace the CT values of the surface voxels. However, the best substitution can be determined based on a controlled experiment. Using both densities, the corrected masses of scanned objects can be compared to their actual masses, and the density that produces the least error can be chosen. An iterative algorithm can also be used to compute a combination of eroded and average densities that produces the mass correction least dependent on object shape or size.

The merging process 346 mentioned above in connection with FIG. 9 will now be described in detail. To avoid combining different objects in a scanned bag, an erosion stage can precede the CCL process. As a result, physically separate objects can be assigned different labels. However, certain explosive devices, such as certain stick-shaped explosive objects, can consist of several explosive objects banded together. The use of erosion can cause each object to be considered separately, thus failing the mass threshold criterion and reducing the overall detection rate. Each of these objects by itself satisfies the density criterion, however, its mass is below the threshold value. In the present invention, a merging process based on the eroded densities of segmented objects can be implemented to recover the objects.

The data show that these objects have almost identical eroded densities as found by the CCL process. In addition, their bounding boxes lay in the same XYZ region. In one embodiment, this information leads to the conclusion that these objects must have been components of the same single object.

In one embodiment, the merging approach deals only with objects within a certain density range that fail the mass threshold criterion. As a result, for every such object the following steps can be performed:

1. Search for an object of similar density, i.e., $$(\bar{\rho}_e)^n = (\bar{\rho}_e)^m + \Delta_m.$$

2. If a density match is found, compute one of the following proximity measures:
   (I.) Bounding box adjacency.
   (ii.) Distances between the centers of bounding boxes; distances can be computed in the XYZ space, XY plane, XZ plane or the YZ plane.
3. Merge the two objects into one if the objects pass the adjacency criterion, i.e., if the distances are less than threshold values.
4. Repeat until merging is not possible.

It should be noted that other criteria such as object location, shape and/or size can be used in determining whether objects should be merged together.

In general, the first step in the explosive detection process of the invention is to detect objects within a given density range. This density range covers most of the objects that can or may be found in luggage. The second step is to eliminate most of these objects based on additional information such as mass. For instance, it may be the case that an explosive will be considered a threat only if its mass exceeds a certain mass threshold.

The mass threshold can be used to have the effect of reducing the false alarm rate. A higher mass threshold yields a lower false alarm and lower detection rate. On the other hand, a lower mass threshold increases both the detection and the false alarm rates. As a compromise, in one embodiment, objects of different densities are subjected to different threshold masses. The mass threshold can then be described by $$M_t = \begin{cases} m_l & \text{if } \rho_{\min}^b \leq \bar{\rho}_e < \rho_t \\ m_h & \text{if } \rho_t \leq \bar{\rho}_e \leq \rho_{\max}^b \end{cases} \quad (26)$$

In accordance with the invention, it has been recognized that different density ranges can be associated with different false alarm rates. As a result, selection of a mass threshold based on a density range can be used to adjust the false alarm rate within that particular density range, which results in an adjustment of the overall system false alarm rate. For example, a density range may be associated with a relatively high false alarm rate. A relatively high mass threshold can be selected for that density range to reduce the false alarm rate for that range. As a result, the overall system false alarm rate is reduced.

Figure 12:
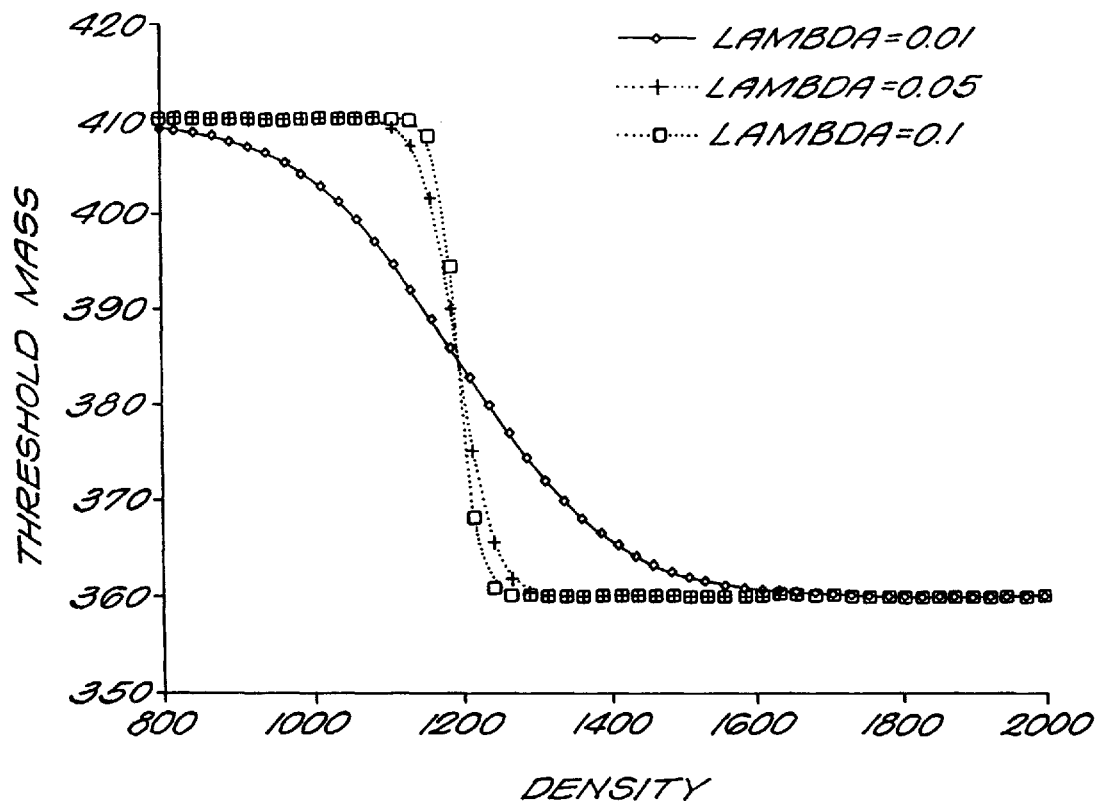
FIG. 12 is a schematic plot of mass threshold versus density illustrating three different density dependent mass thresholds in accordance with the present invention.

Other density dependent threshold masses can be used. For example, the density space can be divided into more than two nonoverlapping regions. Furthermore, the step function can be replaced with a gradual change in mass between two density regions:

$$M_T(\rho) = M_T^1 + \frac{M_T^2 - M_T^1}{1 + \exp\{\lambda(\rho - \rho_T)\}} \quad (27)$$

where $M_T^1$ and $M_T^2$ are the threshold masses in each region, $\rho_T$ is the boundary between the two regions, and $\lambda$ is the transition factor, which determines the width of the transition region between the two threshold masses. The transition factor $\lambda$ can be determined automatically using a set of scanned luggage. FIG. 12 is a schematic plot of mass threshold versus density illustrating three different density dependent mass thresholds.

In one embodiment, the decision made by the two detection methods for sheets and bulks is reconciled in order to reach a unanimous decision. For this purpose, the two label images produced by two parts of the process are fused to obtain a single label file. The inputs to the decision-data fusion method include:

$N_s$, Total number of detected sheet explosives;
$L_s(i,j,k)$, Sheet explosive label image;
$N_b$, Total number of detected bulk explosives; and
$L_b(i,j,k)$, Bulk explosive label image.

The outputs include:

N, Total number of detected explosives; and
L(i,j,k), Fused label image.

In one embodiment, the decision-data fusion process includes the following steps.

1. Check the number of detected sheet explosives, $N_s$ and the number of detected bulk explosives, $N_b$. Both should be non-zero in order to perform the data fusion. Otherwise, take the label image with non-zero explosives.

$$\left.\begin{array}{l} L(i,j,k) = L_s(i,j,k) \\ N = N_s \end{array}\right\} N_s > 0 \text{ and } N_b = 0 \quad (28)$$

$$\left.\begin{array}{l} L(i,j,k) = L_b(i,j,k) \\ N = N_b \end{array}\right\} N_b > 0 \text{ and } N_s = 0$$

2. Fuse the label images, if both $N_s$ and $N_b$ are non-zero.

$$L(i,j,k) = \begin{cases} L_s(i,j,k) + N_b & L_b(i,j,k) = 0 \\ L_b(i,j,k) & \text{Otherwise} \end{cases} \quad (29)$$

It should be noted that if a voxel has two conflicting labels, one of them designating it as part of a sheet object and the other labeling it as a bulk object, then an arbitrary decision is made to use the bulk object label for the voxels. Also, if output specifications for the detection method change, the data fusion part of the method can be switched off, resulting in two separate output label images for sheet and bulk objects.

Several variations and additions can be incorporated in the detection process of the invention. These will now be described in detail.

Running bulk detection first and subtracting the detected objects from the image can be performed to reduce processing time. Bulk detection takes less time than sheet detection. Sheet explosive detection then works only on the remaining voxels, speeding up the overall detection process. That is, in one embodiment, detection is carried out in stages such that the overall detection process is more efficient. Each item that can be identified by the method of the invention is, in general, associated with a unique set of detection steps. In the present invention, a detection approach is applied to eliminate inefficiencies introduced by repetitive processing of the data by multiple detection methods. Where one specific detection procedure has been applied to a set of data and has been used to classify that data, the data are removed from further processing.

Terminating the detection process after detecting the first explosive can also increase the throughput of the system, since the operator inspects the bag images if a potentially explosive object is found.

Execution time limits can be applied to the process. The execution time of the detection process increases significantly if the bag has a large total volume occupied by dense objects. Such a luggage item may be declared suspicious and forwarded for further inspection by an operator without completing all of the detection process steps.

Merging divided sheets by extending their surface planes can be used to improve the sheet detection approach. Sheet explosives may be detected as smaller pieces if they are located near a relatively opaque object such as a metal bar. If they are not merged, each part is eliminated by the mass threshold. One way to merge these pieces in accordance with the invention is to fit a plane to each piece and determine the intersection of the two planes. If the intersection is close (in the predetermined limits) to both the pieces, then both pieces are considered to be part of a bigger sheet, and the mass becomes the total mass of the pieces. As a result, the merged object exceeds the mass threshold and is identified as a threat object.

It may be the case that it is desirable to detect liquid objects. If it has been determined that liquid objects should be classified as non-threat items, then it can be beneficial to identify liquids as such to reduce the number of possible alarms.

Many bags have bottles of liquid (shampoo, water, wine etc.) in them. If these bottles of liquid trigger a false alarm, they can be discriminated using a liquid detection method of the invention and thus reduce the number of false alarms. The liquid detection method distinguishes liquid bottles from solid objects. This detection uses the fact that the surface of a liquid is level with the horizontal, and air is usually above the surface. This assumes that the bottle of liquid is not completely full. Given the bounding box and the voxels of the detected object, the number of voxels touching each surface of the bounding box is determined and the percentage of the top surface count in the total count is computed. A voxel is concluded to touch a surface of the bounding box if it is labeled as being part of the object, i.e., bottle of liquid, and it is also located at or near the surface of the bounding box. If the percentage is larger than a predetermined threshold and the average value of the voxels above the liquid surface is close to air value, then the object is a liquid.

In one embodiment, the invention determines whether an object is a contained liquid by first creating a bounding box which surrounds the object. Along the height of the bounding box, the histogram of the number of top-surface voxels and the histogram of the number of bottom-surface voxels are computed. Here the top-surface voxels are defined as the voxels of the object that are visited first while traversing a column of voxels in the bounding box from top to bottom. The bottom-surface voxels are defined as the voxels of the object that are visited last while traversing a column of voxels in the bounding box from top to bottom. The position of the maximum of the histogram for top-surface voxels defines the location of the top surface along the height of the bounding box and the maximum count in the histogram defines the number of top-surface voxels. Similarly for the bottom-surface histogram, the position of the maximum defines the location of the bottom surface and the maximum count defines the number of bottom-surface voxels. The ratio of the number of top-surface voxels to the top-surface area of the bounding box is calculated. If this ratio exceeds a predetermined threshold, and the ratio of the number of top-surface voxels to the number of bottom-surface voxels exceeds another predetermined threshold, and if the average density of voxels above the top surface indicates that air is located above the top surface, then it is concluded that the object is a contained liquid. In one embodiment, it can then be concluded that the object does not pose a threat.

The overall performance of the system, including detection rate and false alarm rate, can be optimized. The overall detection rate of the many types of explosives depends on their a priori probabilities and the likelihood of detection. The detection likelihood depends on the individual detection processes of each of these explosive types. The detection process may have done very well on one type but not so well on another type of explosive. In one embodiment, the overall detection rate is the average of the individual detection rates. The overall false alarm rate of the system also depends on the individual false alarm rates. In one embodiment, the overall system false alarm rate is the sum of the individual false alarm rates. For example, individual and overall system detection and false alarm rates can be as presented in Table 1 for a particular set of predetermined thresholds and parameters for three separate types of materials labeled, for illustration purposes, as Type 1, Type 2, and Type 3.

TABLE 1

| Item | Detection Rate $P_D(\%)$ | False Alarm Rate $P_{FA}(\%)$ |
|---|---|---|
| Type 1 | 95 | 5 |
| Type 2 | 100 | 15 |
| Type 3 | 100 | 10 |
| Overall System | 98.33 | 30 |

In accordance with the invention, it is recognized that the individual detection rates for the three material types are interrelated. That is, for example, the detection rate for Type 2 materials is affected by the detection rate for Type 1 materials. In addition, as a detection rate is changed, its corresponding false alarm rate also changes.

If, for example, a set of system specifications that requires an overall system detection rate of $P_D \geq 95\%$ and an overall system false alarm rate of $P_{FA} \leq 10\%$, is applied to the system of Table 1, it would not meet the requirements. In accordance with the invention, one or more of the individual detection rates can be adjusted to bring the overall system into compliance. This can be done, for example, by lowering the detection rates of Type 2 and Type 3 materials. An example of the result of this adjustment is shown in Table 2. It is noted that the values in Tables 1 and 2 are used for illustration purposes only and are not intended to reflect actual system parameters.

TABLE 2

| Item | Detection Rate $P_D(\%)$ | False Alarm Rate $P_{FA}(\%)$ |
|---|---|---|
| Type 1 | 95 | 5 |
| Type 2 | 92 | 2 |

TABLE 2-continued

| Item | Detection Rate $P_D(\%)$ | False Alarm Rate $P_{FA}(\%)$ |
|---|---|---|
| Type 3 | 98 | 3 |
| Overall System | 95 | 10 |

As shown, the system is now in compliance with the sample specifications as a result of the adjustment to the two individual detection rates. It is noted that as each detection rate was adjusted down, its associated false alarm rate was also reduced. Hence, given the desired ranges for overall and individual detection rates, the overall detection rate and/or false alarm rate can be optimized by adjusting the individual detection likelihoods and false alarm rates. In one embodiment, the system is tunable to a specific detection rate and/or a specific false alarm rate.

It should be noted that an individual detection rate can be dependent on other individual detection rates. As a result, adjustment of one rate may inadvertently change another rate. To account for this effect, statistical data analysis approaches such as simulated annealing and genetic algorithms can be employed to determine parameters required to adjust the individual rates as required for a particular desired overall system performance.

In the present invention, the detection rates can be adjusted by one or more of several approaches. For example, the extensive analysis performed on actual threat and non-threat items has resulted in a relationship between object density and threat mass threshold. This permits mass thresholds to be tailored to particular densities, and, therefore, to particular threat items. Where it is desired to reduce the detection rate and, therefore, the false alarm rate, of a particular threat, a higher mass threshold for the density range of the particular threat can be employed. In addition to or instead of the adjustment of mass thresholds, other such deterministic parameter adjustment approaches can be employed. That is, other parameters described in detail herein can be adjusted to tailor the individual detection and/or false alarm rates and, consequently, the overall system detection and/or false alarm rates. Also, in addition to or instead of these deterministic approaches, statistical approaches such as simulated annealing and genetic algorithms applied to the data acquired for actual threat and non-threat objects can be used to adjust one or more parameters and/or thresholds to adjust the detection and/or false alarm rates.

Intelligence data can provide additional information regarding possible shapes of explosive devices and their likely locations inside a bag. Statistics on shapes and locations of typical non-threat items carried in checked luggage can be gathered by testing items. This information can be used at the decision making stages of the method to further discriminate between threats and innocuous objects. For example, new discrimination features and/or process changes may be incorporated to account for perishable items.

While this invention has been particularly shown and described with references to preferred embodiments thereof, it will be understood by those skilled in the art that various changes in form and details may be made therein without departing from the spirit and scope of the invention as defined by the following claims. For example, the invention is applicable to detect explosives other than the specific materials disclosed above. Also, the invention is applicable to detect other objects and materials including drugs and currency. The invention can be used to detect any of these items in checked and carried-on luggage and in shipping and other types of containers.

What is claimed is:

1. A method of detecting sheet objects represented in reconstructed computed tomography (CT) data for a region comprising:

identifying a plurality of volume elements in the reconstructed CT data for the region, each volume element being associated with a density value;

performing a sheet voxel identification process on the reconstructed CT data for the region to identify those volume elements associated with any sheet objects represented by the reconstructed CT data for the region and to discriminate those volume elements associated with any sheet objects from volume elements associated with other object shapes; and after performing the sheet voxel identification process, connecting the volume elements identified by the sheet voxel identification process as associated with any sheet objects into sheet objects, wherein performing a sheet voxel identification detection process comprises:

performing a predetermined number N of erosion steps during which volume elements are removed from the reconstructed CT image data for the region, said erosion steps producing eroded CT image data;

identifying an eroded object in the eroded CT image data;

removing the volume elements of the eroded object from the reconstructed CT image data; and labeling an object in the reconstructed CT image data after removal of the eroded object as a sheet object.

2. The method of claim wherein the number N is based on an expected thickness of a sheet object.

3. A method of detecting sheet objects represented in computed tomography (CT) data for a region comprising:

identifying a plurality of volume elements in the CT data for the region, each volume element being associated with a density value;

performing a sheet voxel identification process on the CT data for the region to identify those volume elements associated with any sheet objects represented by the CT data for the region and to discriminate those volume elements associated with any sheet objects from volume elements associated with other object shapes; and after performing the sheet voxel identification process, connecting the volume elements identified by the sheet voxel identification process as associated with any sheet objects into sheet objects; further comprising, for each volume element of interest:

identifying a plurality of neighboring volume elements of the region;

comparing the density value associated with each of the neighboring volume elements with a predetermined object density range;

counting a number of neighboring volume elements whose density values are not within the predetermined object density range;

comparing the number of neighboring volume elements whose density values are not within the predetermined object density range with a predetermined threshold; and if the number of neighboring volume elements whose density values are not within the predetermined object density range exceeds the predetermined threshold, removing the volume element from the object.

4. The method of claim 3 wherein the predetermined object density range is selected such that volume elements at a surface of the object are removed from the object.

5. The method of claim 3 wherein the predetermined object density range is selected such that volume elements at a surface of an interior void region of the object are not removed from the object.

6. A method of detecting sheet objects represented in computed tomography (CT) data for a region comprising:

identifying a plurality of volume elements in the CT data for the region, each volume clement being associated with a density value;

performing a sheet voxel identification process on the CT data for the region to identify those volume elements associated with any sheet objects represented by the CT data for the region and to discriminate those volume elements associated with any sheet objects from volume elements associated with other object shapes; and after performing the sheet voxel identification process, connecting the volume elements identified by the sheet voxel identification process as associated with any sheet objects into sheet objects; further comprising:

computing a distance between a first object and a second object represented in the CT data;

computing a first density associated with the first object and a second density associated with a second object;

computing a difference between the first density and the second density; and combining the first object and the second object into a single combined object if the difference between the first density and the second density is below a predetermined density difference threshold and the distance between the first object and the second object is below a predetermined distance threshold.

7. The method of claim 6 further comprising:

computing a first mass of the first object and a second mass of the second object;

combining the mass of the first and second objects into a combined mass; and classifying the single object according to the combined mass.

8. The method of claim 7 wherein the classifying step comprises:

comparing the combined mass to a predetermined mass threshold; and if the combined mass exceeds the predetermined mass threshold, labeling the single combined object as a threat object.

9. An apparatus for detecting sheet objects represented in reconstructed computed tomography (CT) data for a region, comprising:

a volume element identifier arranged so as to identify a plurality of volume elements in the reconstructed CT data for the region, each volume clement being associated with a density value;

voxel identification processor arranged so as to perform a sheet voxel identification process on the reconstructed CT data for the region to identify those volume elements associated with any sheet objects represented by the reconstructed CT data for the region and to discriminate those volume elements associated with any sheet objects from volume elements associated with other object shapes; and a volume element connector arranged so as to connect the volume elements identified by the voxel identification process as associated with any sheet objects into sheet objects;

wherein the voxel identification processor comprises:
an erosion processor arranged so as to perform a predetermined number N of erosion steps during which volume elements are removed from the reconstructed CT image data for the region, said erosion steps producing eroded CT image data;
an erosion object identifier arranged so as to identify an eroded object in the eroded CT image data;
a volume element remover arranged so as to remove the volume elements of the eroded object from the reconstructed CT image data; and
an object labeler arranged so as to label an object in the reconstruced CT image data after removal of the eroded object as a sheet object.

10. The apparatus of claim 9 wherein the number N is based on an expected thickness of a sheet object.

11. An apparatus for detecting sheet objects represented in computed tomography (CT) data for a region, comprising:
a volume clement identifier arranged so as to identify a plurality of volume elements in the CT data for the region each volume element being associated with a density value;
voxel identification processor arranged so as to perform a sheet voxel identification process on the CT data for the region to identify those volume elements associated with any sheet objects represented by the CT data for the region and to discriminate those volume elements associated with any sheet objects from volume elements associated with other object shapes; and
a volume element connector arranged so as to connect the volume elements identified by the sheet voxel identification process as associated with any sheet objects into sheet objects;
a neighboring volume element identifier arranged so as to identify, for each volume element of interest, a plurality of neighboring volume elements of the region;
a density comparator arranged so as to compare the density value associated with each of the neighboring volume elements with a predetermined object density range;
a counter arranged so as to count a number of neighboring volume elements whose density values are not within the predetermined object density range;
a number comparator arranged so as to compare the number of neighboring volume elements whose density values are not within the predetermined object density range with a predetermined threshold; and
a volume element remover arranged so as to remove the volume element from the object if the number of neighboring volume elements whose density values are not within the predetermined object density range exceeds the predetermined threshold.

12. The apparatus of claim 11 wherein the predetermined object density range is selected such that volume elements at a surface of the object are removed from the object.

13. The apparatus of claim 11 wherein the predetermined object density range is selected such that volume elements at a surface of an interior void region of the object are not removed from the object.

14. An apparatus for detecting sheet objects represented in computed tomography (CT) data for a region, comprising:
a volume element identifier arranged so as to identify a plurality of volume elements in the CT data for the region, each volume element being associated with a density value;
voxel identification processor arranged so as to perform a sheet voxel identification process on the CT data for the region to identify those volume elements associated with any sheet objects represented by the CT data for the region and to discriminate those volume elements associated with any sheet objects from volume elements associated with other object shapes; and
a volume element connector arranged so as to connect the volume elements identified by the sheet voxel identification process as associated with any sheet objects into sheet objects;
a distance computing component arranged so as to compute a distance between a first object and a second object represented in the CT data;
a density computing component arranged so as to compute a first density associated with the first object and a second density associated with a second object;
a difference computing component arranged so as to compute a difference between the first density and the second density; and
an object combiner arranged so as to combine the first object and the second object into a single object if the difference between the first density and the second density is below a predetermined density difference threshold and the distance between the first object and the second object is below a predetermined distance threshold.

15. The apparatus of claim 14 further comprising:
a mass computing component arranged so as to compute a first mass of the first object and a second mass of the second object;
a mass combiner arranged so as to combine the mass of the first and second objects into a combined mass; and
an object classifier arranged so as to classify the single object according to the combined mass.

16. The apparatus of claim 15 wherein the means for classifying the single object according to the combined mass comprises:
a mass comparator arranged so as to compare the combined mass to a predetermined mass threshold; and
an object labeler arranged so as to label the single combined object as a threat object if the combined mass exceeds the predetermined mass threshold.

17. A computed tomography (CT) scanning system for detecting sheet objects in a region comprising:
a volume element identifier arranged so as to identify a plurality of volume elements in reconstructed CT data for the region, each volume element being associated with a density value;
voxel identification processor arranged so as to perform a sheet voxel identification process on the reconstructed CT data for the region to identify those volume elements associated with any sheet objects represented by the reconstructed CT data for the region and to discriminate those volume elements associated with any sheet objects from volume elements associated with other object shapes; and
a volume element connector arranged so as to connect the volume elements identified by the sheet voxel identification process as associated with any sheet objects into sheet objects;
wherein the voxel identification processor comprises:
an erosion processor arranged so as to perform a predetermined number N of erosion steps during which volume elements are removed from the reconstructed CT image data for the region, said erosion steps producing eroded CT image data;

an erosion object identifier arranged so as to identify an eroded object in the eroded CT image data;

a volume element remover arranged so as to remove the volume elements of the eroded object from the reconstructed CT image data; and an object labeler arranged so as to label an object in the reconstructed CT image data after removal of the eroded object as a sheet object.

18. The CT scanning system of claim 17 wherein the number N is based on an expected thickness of a sheet object.

19. A computed tomography (CT) scanning system for detecting sheet objects in a region comprising:

a volume element identifier arranged so as to identify a plurality of volume elements in the CT data for the region, each volume element being associated with a density value;

voxel identification processor arranged so as to perform a sheet voxel identification process on the CT data for the region to identify those volume elements associated with any sheet objects represented by the CT data for the region and to discriminate those volume elements associated with any sheet objects from volume elements associated with other object shapes; and a volume element connector arranged so as to connect the volume elements identified by the sheet voxel identification process as associated with any sheet objects into sheet objects;

a neighboring volume element identifier arranged so as to identify, for each volume element of interest, a plurality of neighboring volume elements of the region;

a density comparator arranged so as to compare the density value associated with each of the neighboring volume elements with a predetermined object density range;

a counter arranged so as to count a number of neighboring volume elements whose density values are not within the predetermined object density range;

a number comparator arranged so as to compare the number of neighboring volume elements whose density values are not within the predetermined object density range with a predetermined threshold; and a volume element remover arranged so as to remove the volume element from the object if the number of neighboring volume elements whose density values are not within the predetermined object density range exceeds the predetermined threshold.

20. The CT scanning system of claim 19 wherein the predetermined object density range is selected such that volume elements at a surface of the object are removed from the object.

21. The CT rscanning system of claim 19 wherein the predetermined object density range is selected such that volume elements at a surface of an interior void region of the object are not removed from the object.

22. A computed tomography (CT) scanning system for detecting sheet objects in a region comprising:

a volume element identifier arranged so as to identify a plurality of volume elements in the CT data for the regions each volume element being associated with a density value;

voxel identification processor arranged so as to perform a sheet voxel identification process on the CT data for the region to identify those volume elements associated with any sheet objects represented by the CT data for the region and to discriminate those volume elements associated with any sheet objects from volume elements associated with other object shapes; and a volume element connector arranged so as to connect the volume elements identified by the sheet voxel identification process as associated with any sheet objects into sheet objects a distance computing component arranged so as to compute a distance between a first object and a second object represented in the CT data;

a density computing component arranged so as to compute a first density associated with the first object and a second density associated with a second object;

a difference computing component arranged so as to compute a difference between the first density and the second density; and an object combiner arranged so as to combine the first object and the second object into a single object if the difference between the first density and the second density is below a predetermined density difference threshold and the distance between the first object and the second object is below a predetermined distance threshold.

23. The CT scanning system of claim 22 further comprising:

a mass computing component arranged so as to compute a first mass of the first object and a second mass of the second object;

a mass combiner arranged so as to combine the mass of the first and second objects into a combined mass; and an object classifier arranged so as to classify the single object according to the combined mass.

24. The CT scanning system of claim 23 wherein the means for classifying the single object according to the combined mass comprises:

a mass comparator arranged so as to compare the combined mass to a predetermined mass threshold; and an object labeler arranged so as to label the single combined object as a threat object if the combined mass exceeds the predetermined mass threshold.

* * * * *

UNITED STATES PATENT AND TRADEMARK OFFICE
CERTIFICATE OF CORRECTION

PATENT NO. : 6,317,509 B1
DATED : November 13, 2001
INVENTOR(S) : Sergey Simanovsky et al.

It is certified that error appears in the above-identified patent and that said Letters Patent is hereby corrected as shown below:

<u>Column 37, claim 2,</u>
Line 33, after "claim", insert -- 1 --.

Signed and Sealed this

Nineteenth Day of March, 2002

Attest:

JAMES E. ROGAN
*Director of the United States Patent and Trademark Office*

*Attesting Officer*